US006498027B1

(12) United States Patent
Van Es et al.

(10) Patent No.: US 6,498,027 B1
(45) Date of Patent: Dec. 24, 2002

(54) TARGETED DELIVERY THROUGH A CATIONIC AMINO ACID TRANSPORTER

(75) Inventors: Helmuth Van Es, Hoofddorp; Menzo Jans Emco Havenga, Alphen aan den Rijn; Stefan Frederik Franciscus Verlinden, Leiden, all of (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 09/315,926

(22) Filed: May 20, 1999

(30) Foreign Application Priority Data

May 20, 1998 (EP) .............................. 98201693

(51) Int. Cl.⁷ ..................... C12N 7/01; C12N 15/861; C12N 15/867; C07K 7/04; C07K 7/08
(52) U.S. Cl. ................ 435/235.1; 435/69.1; 435/320.1; 435/455; 435/456; 530/327; 530/328; 530/329; 530/330; 530/326; 530/350
(58) Field of Search .............................. 435/69.1, 235.1, 435/320.1, 455, 456; 514/2, 44; 424/450, 93.1, 93.2, 93.6; 530/327, 350, 328, 329, 330, 326

(56) References Cited

FOREIGN PATENT DOCUMENTS

WO    WO 97/00326    1/1997

*Primary Examiner*—David Guzo
(74) *Attorney, Agent, or Firm*—TraskBritt

(57) ABSTRACT

The invention relates to the targeted delivery of substances to cells. The invention provides a virus-like particle or gene delivery vehicle provided with a ligand capable of binding to a human amino acid transporter. Provided are, for example, ligands that can bind to the human transporter of cationic L-amino acids (hCAT1). Such hCAT1 binding molecules find applications in the design of vector systems for entry into human or primate cells. Preferred are retroviral envelope molecules, which—when incorporated in a virus particle—can infect hCAT1 positive cells at high frequencies. Also disclosed are methods for the design of such hCAT1 binding molecules.

12 Claims, 27 Drawing Sheets

Figure 3b

Sequencing third extracellular domain hCAT1 cDNA
isolated from human CD34+ hemopoietic cells,

```
AAA AAC TGG CAG CTC ACG GAG GAT TTT GGG AAC ACA TCA GGC CGT CTC   (1)
AAA AAC TGG CAG CTC ACG GAG GAT TTT GGG AAC ACA TCA GGC CGT CTC   (2)
AAA AAC TGG CAG CTC ACG GAG GAT TTT GGG AAC ACA TCA GGC CGT CTC   (3)
AAA AAC TGG CAG CTC ACG GAG GAT TTT GGG AAC ACA TCA GGC CGT CTC   (4)
 K   N   W   Q   L   T   E   D   F   G   N   T   S   G   R   L

TGT TTG AAC AAT GAC ACA AAA GAA GGG AAG CCC GGT GTT GGT GGA TTC   (1)
TGT TTG AAC AAT GAC ACA AAA GAA GGG AAG CCC GGT GTT GGT GGA TTC   (2)
TGT TTG AAC AAT GAC ACA AAA GAA GGG AAG CCC GGT GTT GGT GGA TTC   (3)
TGT TTG AAC AAT GAC ACA AAA GAA GGG AAG CCC GGT GTT GGT GGA TTC   (4)
 C   L   N   N   D   T   K   E   G   K   P   G   V   G   G   F
```

1: hCAT1 sequence from human lymphocytes (Yoshimoto et al,1991)
2,3: Sequence of hCAT1 from CD34+ cells isolated from mobilized peripheral blood
3: Sequence of hCAT1 from CD34+ cells isolated from umbillical cord blood

Northern blot analysis of cell lines with hCAT1 probe 1) 911-pcDNA3
2) 911-hCAT1 k08
3) 911
4) 911-hCAT1 pool 1    2    3    4

Binding of cloned 12 mer peptide displaying phages to hCAT1 peptide as measured by ELISA Binding of SVSVGMKPSPRP displaying phage measured by flow cytometry Binding of cloned human FAb displaying phages to hCAT1 peptide as measured by ELISA

Figure 12

Binding of cloned human FAb displaying phages to hCAT1 expressing cells determined by flow cytometry

| Phage: | Median 911-pcDNA3: | Median 911-hCAT1: |
|---|---|---|
| 1 | 2,27 | 2,79 |
| 2 | 3,62 | 4,22 |
| 3 | 16,7 | 13,46 |
| 4 | 21,29 | 18,27 |
| 5 | 11,44 | 12,41 |
| 6 | 11,86 | 8,82 |
| 7 | 12,98 | 8,82 |
| 8 | 12,3 | 8,35 |
| 11 | 10,18 | 8,2 |
| 12 | 17,62 | 17 |
| 18 | ND | 8,98 |
| 19 | 7,64 | 12,08 |
| 25 | 11,55 | 10,84 |
| 33 | 13,1 | 11,76 |
|  | 161,08 | 151,25 |
|  | 11,76 | 10,27 |

Example FAb phage clone #25 binding to hCAT1 peptide and hCAT1 expressing unfixed cells

Binding of FAb phage clone #25 to hCAT1 overexpressing cells

Average ratio ± SD : 1.6 ± 1.2 fold, n=10

Vector pCES1 used for construction of human FAb display library

```
GA CGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAA
ATGCTTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTG
GTGAAAGTAAAAGATGCTGAAGATCAGTTGGGTGCCCGAGTGGGTTACATCGAACTG
GATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGG
CAAGAGCAACTCGGTCGCCGCATACACTATTCTCAGAATGACTTGGTTGAGTACTCA
CCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGA
CCGAAGGAGCTAACCGCTTTTTTGCACAACATGGGGGATCATGTAACTCGCCTTGAT
CGTTGGGAACCGGAGCTGAATGAAGCCATACCAAACGACGAGCGTGACACCACGATG
CCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTT
CTGCGCTCGGCCCTTCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCA
TATATACTTTAGATTGATTTAAAACTTCATTTTAATTTAAAAGGATCTAGGTGAAG
ATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAG
CGGTCGGGCTGAACGGGGGGTTCGTGCATACAGCCCAGCTTGGAGCGAACGACCTAC
ACCGAACTGAGATACCTACAGCGTGAGCATTGAGAAAGCGCCACGCTTCCCGAAGGG
AGAAAGGCGGACAGGTATCCGGTAAGCGGCAGGGTCGGAACAGGAGAGCGCACGAGG
GAGCTTCCAGGGGGAAACGCCTGGTATCTTTATAGTCCTGTCGGGTTTCGCCACCTC
TGACTTGAGCGTCGATTTTTGTGATGCTCGTCAGGGGGCGGAGCCTATGGAAAAAC
GCCAGCAACGCGGCCTTTTTACGGTTCCTGGCCTTTTGCTGGCCTTTTGCTCACATG
TTCTTTCCTGCGTTATCCCCTGATTCTGTGGATAACCGTATTACCGCCTTTGAGTGA
GCTGATACCGCTCGCCGCAGCCGAACGACCGAGCGCAGCGAGTCAGTGAGCGAGGAA
GCGGAAGAGCGCCCAATACGCAAACCGCCTCTCCCCGCGCGTTGGCCGATTCATTAA
TGCAGCTGGCACGACAGGTTTCCCGACTGGAAAGCGGGCAGTGAGCGCAACGCAATT
AATGTGAGTTAGCTCACTCATTAGGCACCCCAGGCTTTACACTTTATGCTTCCGGCT
                                                  fab01
CGT ATG TTG TGT GGA ATT GTG AGC GGA TAA CAA TTT CAC ACA
```

Figure 16A

```
                                        HindIII
GGA AAC AGC TAT GAC CAT GAT TAC GCC AAG CTT TGG AGC CTT
▶            ▶ M   T   M   I   T   P   S   F   G   A   F
TTT TTT GGA GAT TTT CAA CGT GAA AAA ATT ATT ATT CGC AAT
▶ F   L   E   I   F   N   V   K   K   L   L   F   A   I
                                                    VL
TCC TTT AGT TGT TCC TTT CTA TTC TCA CAG TGC ACT TGA AAC
▶ P   L   V   V   P   F   Y   S   H   S   A   L   E   T
GAC ACT CAC GCA GTC TCC AGG CAT CCT GTC TTT GTC TCC GGG
▶ T   L   T   Q   S   P   G   I   L   S   L   S   P   G
GGC AGG AGC CAC CCT CTC CTG CAG GGC CAG TCA GAG TGT CAG
                                        ◀
▶ A   G   A   T   L   S   C   R   A   S   Q   S   V   S
  CDR1
CAG CAG GAA CTT AGC CTG GTA CCA GCA GAA ACC TGG CCA GGC
                            ▶
▶ S   R   N   L   A   W   Y   Q   Q   K   P   G   Q   A
                                    CDR2
TCC CAG GCT CCT CAT CTA TGG TGT ATC AAC AGG CAC TGG
                ◀                           ▶
▶ P   R   L   L   I   Y   G   V   S   N   R   A   T   G
CGT CCC AGA CAG GTT CAG TGG CAG TGG GTC TGG GGC AGA CTT
▶ V   P   D   R   F   S   G   S   G   S   G   A   D   F
CAC TCT CAC CAT CAA CAG ACT GGA GCC TGA AGA TTT TGC GGT
▶ T   L   T   I   N   R   L   E   P   E   D   F   A   V
                                        CDR3
GTA TTA CTG TCA GCG GTA TGG CAG GTC ACT GTG GAC GTT CGG
                        ◀
▶ Y   Y   C   Q   R   Y   G   R   S   L   W   T   F   G
TCA AGG GAC CAA GGT GGA GAT CAA ACG TGG AAC TGT GGC TGC
    ▶
▶ Q   G   T   K   V   E   I   K   R   G   T   V   A   A
ACC ATC TGT CTT CAT CTT CCC GCC ATC TGA TGA GCA GTT GAA
▶ P   S   V   F   I   F   P   P   S   D   E   Q   L   K
                    Vl reverse
ATC TGG AAC TGC CTC TGT TGT GTG CCT GCT GAA TAA CTT CTA
                                            ◀
▶ S   G   T   A   S   V   V   C   L   L   N   N   F   Y
```

Figure 16B

```
                                              CL region
        TCC CAG AGA GGC CAA AGT ACA GTG AAA GGT GGA TAA CGC CCT
     ▶   P   R   E   A   K   V   Q   W   K   V   D   N   A   L
        CCA ATC GGG TAA CTC CCA GGA GAG TGT CAC AGA GCA GGA CAG
     ▶   Q   S   G   N   S   Q   E   S   V   T   E   Q   D   S
        CAA GGA CAG CAC CTA CAG CCT CAG CAG CAC CCT GAC GCT GAG
     ▶   K   D   S   T   Y   S   L   S   S   T   L   T   L   S
        CAA AGC AGA CTA CGA GAA ACA CAA AGT CTA CGC CTG CGA AGT
     ▶   K   A   D   Y   E   K   H   K   V   Y   A   C   E   V
                                                      Vh forward
        CAC CCA TCA GGG CCT GAG TTC ACC GGT GAC AAA GAG CTT CAA
     ▶   T   H   Q   G   L   S   S   P   V   T   K   S   F   N
                      AscI
        CAG GGG AGA GTG TTA ATA AGG CGC GCC AAT TCT ATT TCA AGG
        ─────────────▶        •   •
     ▶   R   G   E   C
        AGA CAG TCA T A ATG AAA TAC CTA TTG CCT ACG GCA GCC GCT
                      ▶  M   K   Y   L   L   P   T   A   A   A
                        SfiI                                VH
        GGA TTG TTA TTA CTC GCG GCC CAG CCG GCC ATG GCC CAG GTC
     ▶   G   L   L   L   L   A   A   Q   P   A   M   A   Q   V
        CAG CTG GTG CAG TCT GGG GGA GGC GTG GTC CAG CCT GGG AGG
     ▶   Q   L   V   Q   S   G   G   G   V   V   Q   P   G   R
        TCC CTG AGA CTC TCC TGT GCA GCC TCT GGA TTC ACC TTC AGT
     ▶   S   L   R   L   S   C   A   A   S   G   F   T   F   S
                                                      ◀─────────
     CDR1
        AGC TAT GCT ATG CAC TGG GTC CGC CAG GCT CCA GGC AAG GGG
     ▶   S   Y   A   M   H   W   V   R   Q   A   P   G   K   G
        ────────────────▶
                                          CDR2
        CTG GAG TGG GTG GCA GTT ATA TCA TAT GAT GGA AGC AAT AAA
     ▶   L   E   W   V   A   V   I   S   Y   D   G   S   N   K
                            ◀───────────────────────────────────▶
        TAC TAC GCA GAC TCC GTG AAG GGC CGA TTC ACC ATC TCC AGA
     ▶   Y   Y   A   D   S   V   K   G   R   F   T   I   S   R
        GAC AAT TCC AAG AAC ACG CTG TAT CTG CAA ATG AAC AGC CTG
     ▶   D   N   S   K   N   T   L   Y   L   Q   M   N   S   L
        AGA GCT GAG GAC ACG GCT GTG TAT TAC TGT GCG AGA GGG ATT
     ▶   R   A   E   D   T   A   V   Y   Y   C   A   R   G   I
                                                ◀───────────────
```

Figure 16C

CDR3
         ACA GTA ACT AAA TCA CGA TTT GAC TAC TGG GGC CAG GGC ACC
    ▶     T   V   T   K   S   R   F   D   Y   W   G   Q   G   T
         ────────────────────────────────────▶
         BstEII
         CTG GTC ACC GTC TCA AGC GCC TCC ACC AAG GGC CCA TCG GTC
    ▶     L   V   T   V   S   S   A   S   T   K   G   P   S   V
         TTC CCC CTG GCA CCC TCC TCC AAG AGC ACC TCT GGG GGC ACA
    ▶     F   P   L   A   P   S   S   K   S   T   S   G   G   T
         Vh reverse
         GCG GCC CTG GGC TGC CTG GTC AAG GAC TAC TTC CCC GAA CCG
    ▶     A   A   L   G   C   L   V   K   D   Y   F   P   E   P
         ◀────────────────────────────────
                                                              CH1 region
         GTG ACG GTG TCG TGG AAC TCA GGC GCC CTG ACC AGC GGC GTC
    ▶     V   T   V   S   W   N   S   G   A   L   T   S   G   V
         CAC ACC TTC CCG GCT GTC CTA CAG TCC TCA GGA CTC TAC TCC
    ▶     H   T   F   P   A   V   L   Q   S   S   G   L   Y   S
         CTC AGC AGC GTA GTG ACC GTG CCC TCC AGC AGC TTG GGC ACC
    ▶     L   S   S   V   V   T   V   P   S   S   S   L   G   T
         CAG ACC TAC ATC TGC AAC GTG AAT CAC AAG CCC AGC AAC ACC
    ▶     Q   T   Y   I   C   N   V   N   H   K   P   S   N   T
                                                      NotI
         AAG GTG GAC AAG AAA GTT GAG CCC AAA TCT TGT GCG GCC GCA
    ▶     K   V   D   K   K   V   E   P   K   S   C   A   A   A
         His Tag
         CAT CAT CAT CAC CAT CAC GGGGCCGCAGAACAAAAACTCATCTCAGAAGAG
    ▶     H   H   H   H   H   H
         GATCTGAATGGGGCCGCATAGACTGTTGAAAGTTGTTTAGCAAAACCTCATACAGAA
                         fab02
         AATTCATTTACTAACGTCTGGAAAGACGACAAAACTTTAGATCGTTACGCTAACTAT
                                                    ◀─────────
         GAGGGCTGTCTGTGGAATGCTACAGGCGTTGTGGTTTGTACTGGTGACGAAACTCAG
         TGTTACGGTACATGGGTTCCTATTGGGCTTGCTATCCCTGAAAATGAGGGTGGTGGC
         TCTGAGGGTGGCGGTTCTGAGGGTGGCGGTTCTGAGGGTGGCGGTACTAAACCTCCT
         GAGTACGGTGATACACCTATTCCGGGCTATACTTATATCAACCCTCTCGACGGCACT
         TATCCGCCTGGTACTGAGCAAAACCCCGCTAATCCTAATCCTTCTCTTGAGGAGTCT
         CAGCCTCTTAATACTTTCATGTTTCAGAATAATAGGTTCCGAAATAGGCAGGGTGCA
         TTAACTGTTTATACGGGCACTGTTACTCAAGGCACTGACCCCGTTAAAACTTATTAC
         CAGTACACTCCTGTATCATCAAAAGCCATGTATGACGCTTACTGGAACGGTAAATTC
         AGAGACTGCGCTTTCCATTCTGGCTTTAATGAGGATCCATTCGTTTGTGAATATCAA
         GGCCAATCGTCTGACCTGCCTCAACCTCCTGTCAATGCTGGCGGCGGCTCTGGTGGT
         GGTTCTGGTGGCGGCTCTGAGGGTGGCGGCTCTGAGGGTGGCGGTTCTGAGGGTGGC
         GGCTCTGAGGGTGGCGGTTCCGGTGGCGGCTCCGGTTCCGGTGATTTTGATTATGAA
         AAAATGGCAAACGCTAATAAGGGGGCTATGACC GAA AAT GCC GAT GAA AAC
         GCG CTA CAG TCT GAC GCT AAA GGC AAA CTT GAT TCT GTC GCT

Figure 16D

```
ACT GAT TAC GGT GCT GCT ATC GAT GGT TTC ATT GGT GAC GTT
TCC GGC CTT GCT AAT GGT AAT GGT GCT ACT GGT GAT TTT GCT
GGC TCT AAT TCC CAA ATG GCT CAA GTC GGT GAC GGT GAT AAT
TCA CCT TTA ATG AAT AAT TTC CGT CAA TAT TTA CCT TCT TTG
CCT CAG TCG GTT GAA TGT CGC CCT TAT GTC TTT GGC GCT GGT
AAA CCA TAT GAA TTT TCT ATT GAT TGT GAC AAA ATA AAC TTA
TTC CGT GGT GTC TTT GCG TTT CTT TTA TAT GTT GCC ACC TTT
ATG TAT GTA TTT TCG ACG TTT GCT AAC ATA CTG CGT AAT AAG
GAG TCT AAT AAA GAA TTC ACT GGC CGT CGT TTT ACA ACG TCG
TGA CTG GGA AAA CCC TGG CGT TAC CCA ACT TAA TCG CCT TGC
AGC ACA TCC CCC TTT CGC CAG CTG GCG TAA TAG CGA AGA GGC
CCG CAC CGA TCG CCC TTC CCA ACA GTT GCG CAG CCT GAA TGG
CGA ATG GCG CCT GAT GCG GTA TTT TCT CCT TAC GCA TCT GTG
CGG TAT TTC ACA CCG CAT ATA AAT TGT AAA CGT TAA TAT TTT
GTT AAA ATT CGC GTT AAA TTT TTG TTA AAT CAG CTC ATT TTT
TAA CCA ATA GGC CGA AAT CGG CAA AAT CCC TTA TAA ATC AAA
AGA ATA GCC CGA GAT AGG GTT GAG TGT TGT TCC AGT TTG GAA
CAA GAG TCC ACT ATT AAA GAA CGT GGA CTC CAA CGT CAA AGG
GCG AAA AAC CGT CTA TCA GGG CGA TGG CCC ACT ACG TGA ACC
ATC ACC CAA ATC AAG TTT TTT GGG GTC GAG GTG CCG TAA AGC
ACT AAA TCG GAA CCC TAA AGG GAG CCC CCG ATT TAG AGC TTG
ACG GGG AAA GCC GGC GAA CGT GGC GAG AAA GGA AGG GAA GAA
AGC GAA AGG AGC GGG CGC TAG GGC GCT GGC AAG TGT AGC GGT
CAC GCT GCG CGT AAC CAC CAC ACC CGC CGC GCT TAA TGC GCC
GCT ACA GGG CGC GTA CTA TGG TTG CTT TGA CGG GTG CAG TCT
CAG TAC AAT CTG CTC TGA TGC CGC ATA GTT AAG CCA GCC CCG
ACA CCC GCC AAC ACC CGC TGA CGC GCC CTG ACG GGC TTG TCT
GCT CCC GGC ATC CGC TTA CAG ACA AGC TGT GAC CGT CTC CGG
GAG CTG CAT GTG TCA GAG GTT TTC ACC GTC ATC ACC GAA ACG
CGC GA
```

Figure 16E

Binding of soluble FAb fragments to hCAT1 expressing cells

TARGETED DELIVERY THROUGH A CATIONIC AMINO ACID TRANSPORTER

TECHNICAL FIELD

The invention relates to the targeted delivery of substances to cells.

BACKGROUND

Delivery of substances to cells allows specific treatment of the cells with compounds that act in the targeted cell. For example, tumor cells, when targeted with toxic components, selectively die when the toxin is delivered to the cell. Yet other cells, when provided with a gene lacking in the cell, can be restored in their function, which is so-called "gene therapy".

Delivery of a compound to a cell preferably occurs with a vehicle or particle that effectively brings the compound to the desired cell or cells and then delivers the compound into that cell (in vivo or in vitro) where it can exert its action. For this purpose, particles such as virus-like particles are suited. These particles, often derived from known viruses, such as retrovirus or adenovirus, are small enough to penetrate in-between tissues and cells and arrive at a cell of choice where it can, for example, fuse with the cell and deliver its compound. The virus-like particles may or may not be infectious in themselves; their main concern is the targeted delivery of the compound of interest, such as a gene, a toxin or immuno-stimulating components such as antigens.

Yet other examples are gene-delivery vehicles, specifically designed to transfer a gene to a cell of interest. Virus-like particles capable of delivering a gene are examples of gene-delivery vehicles; however, other examples of such vehicles, of non-viral origin, exist, such as liposomes or microbodies, or even latex particles. Vehicles such as liposomes or microbodies can, of course, also carry compounds other than a gene; in particular, toxic or immuno-stimulating components such as antigens can be included in such a vehicle.

These vehicles or particles all have in common that they are provided with a molecule or fragment thereof (ligand) capable of binding with the targeted cell, allowing targeting of the particle or vehicles to cells. A need exists for specific or broadly applicable ligands that react with cell-surface receptors on cells. In particular, a need exists for ligands that react with cell-surface receptors after which efficient transfer of the compound to the cell, such as a gene, is possible. Especially in human medicine, such a ligand would enable better application of gene-transfer therapy than is possible now.

It has been a long-standing objective to exploit retrovirus technology in human gene therapy applications. However, the infection spectrum of retroviruses limits the applications of these viruses in such applications. All known env variants have a rather broad infection spectrum in common. Herein lies one of the major shortcomings of current recombinant retrovirus technology. For the purpose of gene therapy, retroviruses are very useful vehicles for the transfer of therapeutic sequences if proper ligand-receptor targets are available.

In conclusion, the concept of the use of retroviruses in human gene therapy is well documented (Gordon and Anderson, 1994; Havenga et al., 1997; Vile et al., 1996). However, it would be clearly advantageous and desirable to devise a strategy for targeted delivery of retroviruses, and modification of the infection spectrum.

DESCRIPTION OF THE INVENTION

The invention relates to the targeted delivery of substances to cells. Specifically, the invention includes a virus-like particle or gene delivery vehicle provided with a ligand capable of binding to a human amino acid transporter. Included are, for example, ligands that can bind to the human transporter of cationic L-amino acids ("hCAT1"). Such hCAT1 binding molecules find applications in the design of vector systems for entry into, for example, human or primate cells. Preferred are retroviral envelope molecules, which—when incorporated in a virus particle—can infect hCAT1 positive cells at high frequencies. The invention also includes methods for the design of such hCAT1 binding molecules.

BRIEF DESCRIPTION OF THE FIGURES

FIG. 12 is a bar graph depicting the binding of cloned human FAb displaying phages to hCAT1 expressing cells determined by flow cytometry.

FIG. 16 depicts the sequence of clone 25 (SEQ. ID. No. 77, 78 and 79).

DETAILED DESCRIPTION OF THE INVENTION

Figure 1:
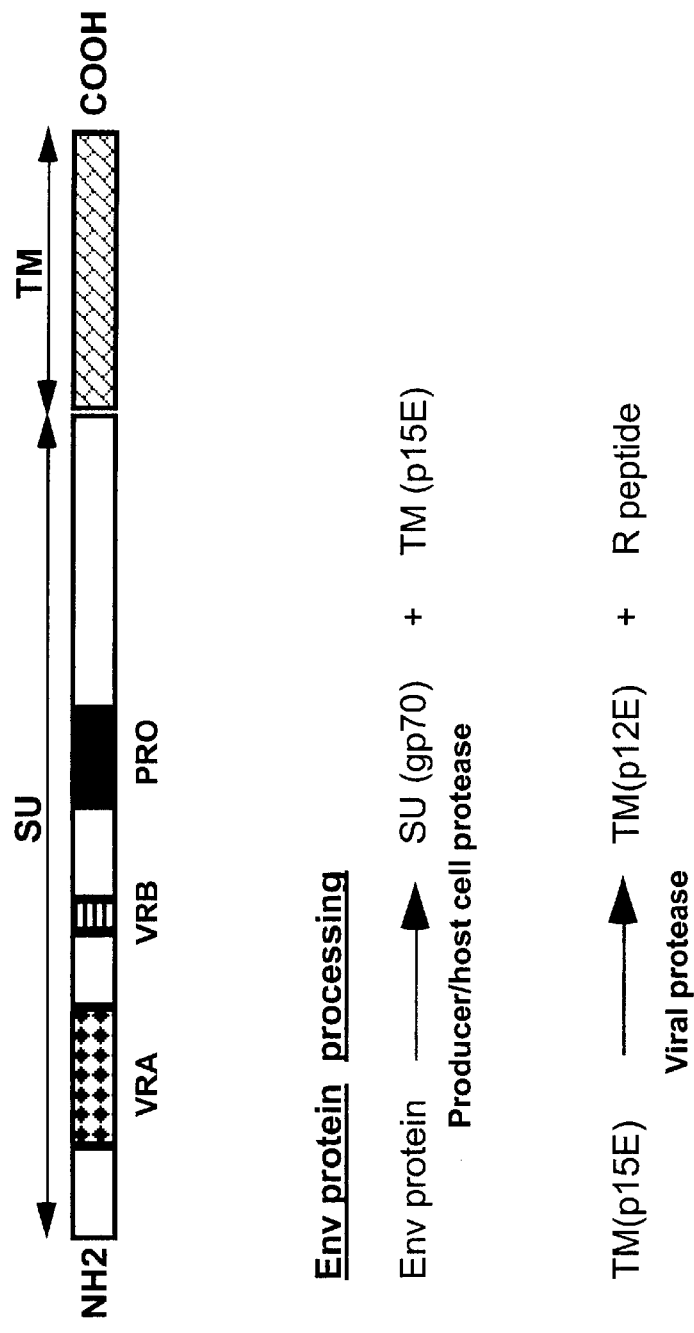
FIG. 1 graphically depicts the organization of ecotropic Moloney murine leukemia retrovirus.

The invention provides a virus-like particle or gene delivery vehicle provided with a ligand capable of binding to a human amino acid transporter. The invention provides the particle or vehicles wherein the ligand includes peptide molecules or fragments thereof binding the transporter, for example, to hCAT1. The peptides or fragments thereof can bind to, for example, the third extracellular domain of the cationic amino acid transporter hCAT1 or to cells expressing this domain of hCAT1 protein on their extracellular cell surface. These hCAT1 binding molecules can be peptides or antibody fragments displayed on a filamentous phage or as free molecules. In a preferred embodiment, the invention provides a virus-like particle or gene delivery vehicle for delivery of genes to human cells; however, it is also possible to provide the particles or vehicles with other compounds, such as toxins for selective killing or antigens for immunization.

In a particular embodiment of the invention, a virus-like particle or gene delivery vehicle is provided including at least one viral protein provided with the ligand. Included in the present invention is the use of hCAT1 binding ligands to provide a particle or vehicle that employs hCAT1 to enter a hemopoietic stem cell or any other cell expressing hCAT1. hCAT1 ligands can be incorporated in the envelope of a retrovirus or the capsid of any other viral or non-viral gene transfer vehicle such as an adenoviral vector. Incorporation of these hCAT1 binding sequences can be done using techniques known in the art.

The invention provides a virus-like particle or gene delivery vehicle wherein the viral protein includes an envelope protein. In a preferred embodiment, the invention provides a mutant retroviral envelope that is derived from a wild-type ecotropic envelope and which employs hCAT1 to enter the human or primate cell by binding to hCAT1. Such a new retroviral envelope molecule, when incorporated in a retroviral virion, will be able to infect hCAT1 positive cells such as human PHSCs at high efficiencies. The mutant retroviral envelopes can be used to pseudotype recombinant type C retrovirus including, but not limited to murine leukemia retroviral vectors. In a further embodiment of the present invention, these hCAT1 binding envelopes can also be used to pseudotype lentiviral vectors including equine or HIV derived lentiviral vectors (Kim et al., 1998; Rizvi and Panganiban, 1992),(Kafri et al., 1997; Poeschla et al., 1996), (Miyoshi et al., 1997; Naldini et al., 1996b). Any hCAT1 ligands or binding envelope molecules or parts thereof made according to the methods described herein or other methods can be ligated into full length mammalian retroviral envelope expression constructs and introduced in cell lines expressing and containing all the sequences necessary for the generation of infectious and functional retroviral particles; in a preferred embodiment, the invention provides a virus-like particle or gene delivery vehicle derived from a retrovirus.

In yet another embodiment, the invention provides a virus-like particle or gene delivery vehicle wherein the viral protein includes a capsid protein. hCAT1 binding sequences or ligands can also be incorporated in the capsid proteins of an adenovirus including, but not limited to, the HI loop of the knob domain of an adenovirus (Krasnykh et al., 1998), preferably an adenovirus which does not bind to the adenoviral receptor CAR1 or MHC1. This results in an adenovirus that enters cells through hCAT1. Deduced from mCAT1 absent expression in mouse liver (Closs et al., 1993), an hCAT1 binding adenovirus does not exhibit liver transduction when administered in vivo. By combining an hCAT1 targeted knob with a ligand for another in vivo target hCAT1, targeting of an adenovirus can remove an important limitation of in vivo use of adenoviral vectors for gene therapy (Sullivan et al., 1997). In another embodiment an hCAT1 targeted adenovirus will more efficiently transduce cells that are difficult to transduce, such as endothelial cells or smooth muscle cells, as compared to a wild-type adenoviral vector including, but not limited, to an adenoviral vector derived from the adenoviral serotype 5. The invention also provides a virus-like particle or gene delivery vehicle derived from an adenovirus.

An hCAT1 targeted adenovirus is useful for local applications of adenoviral vector such as in patients with restenosis following balloon angioplasty where smooth muscle cells need to be transduced with, for example, an adenoviral vector carrying the ceNOS cDNA. More efficient transduction of these tissues results in lower multiplicities of infections (MOIs) that can be used and therefore, less vector associated toxicity to the tissues surrounding the target cells (PCT/EP98/00723).

In a preferred embodiment, the invention provides a virus-like particle or gene delivery vehicle according to the invention wherein the amino acid transporter is a cationic amino acid transporter, preferably a human cationic amino acid transporter-1 (hCAT1). In a preferred example of the invention, the invention provides a virus-like particle or gene delivery vehicle wherein the ligand includes an amino acid sequence selected from Table 2, preferably from the last four different sequences of Table 2 or a sequence functionally related thereto. Various examples of a ligand having hCAT1 binding activity are provided; a particularly strong example is a ligand including at least a part of, including minimally 5, more preferably minimally 7 amino acids of the amino acid sequence SVSVGMKPSPRP (SEQ. ID. No. 1).

In yet another embodiment, the invention provides a virus-like particle or gene delivery vehicle according to the invention wherein the ligand includes a fragment derived from a phage displaying at least one antibody fragment selected for its capacity to bind with the amino acid transporter. In particular, a virus-like particle or gene delivery vehicle is provided wherein the antibody fragment includes an amino acid sequence as shown in FIG. 16 or an amino acid sequence functionally equivalent thereto or obtainable by a method as described herein.

The invention also provides use of a virus-like particle or gene delivery vehicle according to the invention in gene-transfer therapy. In numerous gene therapy applications, targeted delivery of genes into defined cells is provided by the invention, most notably in the case of in vitro gene transfer into cell types present with low abundance in cell mixtures and in approaches for in vivo gene transfer into cells in a living animal body. In a particular embodiment, the particles or vehicles provided by the invention are used for gene therapy using hCAT1 mediated gene transfer including but not limited to mammalian smooth muscle cells or hemopoietic stem cells such as CD34+CD38− or CD34+ (CD33CD38CD71)−cells, including but not limited to adenoviral or retroviral gene transfer vehicles.

The invention also provides a method for selecting a filamentous phage expressing a protein capable of binding to a ligand including constructing a phage library, enriching the library for phages having desired binding characteristics by at least one round of selection of phages for their capacity to bind to a synthetic peptide derived from the ligand, and further including enriching the library for phages having desired binding characteristics by at least one round of selection of phages for their capacity to bind to a cell expressing the ligand.

The invention, for example, provides a peptide phage display to select hCAT1 binding peptides for incorporation in a ligand. To isolate peptides that bind to the third extracellular domain, we employed peptide phage display. A 12 mer peptide phage display library was purchased from New England Biolabs. This library is constructed in the filamentous E. coli phage m13 and the peptide sequences are displayed as N-terminal fusion proteins with the minor coat protein pIII. The unamplified library had a complexity of $1.9 \times 10^9$ different sequences as determined by the suppliers. We amplified the library once before using it to select hCAT1 binding peptide phages. Two targets were used to select for peptide displaying phages which bind to the third extracellular domain of hCAT1. First, the predicted third extracellular domain of hCAT1 was synthesized as a synthetic peptide by Neosystem, Strasbourg, France. The N-terminus of this peptide was biotinylated and followed by three amino acid linker residues KRR, followed by the predicted sequence of the third extracellular domain. Second, we generated cell lines derived from the human 911 cell line that over-express hCAT1 as judged by steady-state mRNA expression levels. The hCAT1 expression construct hATRCC1 which, is a pcDNA3 based expression construct of the hCAT1 cDNA, was employed to transfect 911 cell lines followed by selection for neomycin resistance. A cloned cell line designated k08 was isolated which expresses high levels of hATRCC1 derived hCAT1 mRNA.

Retroviruses are RNA viruses which efficiently integrate their genetic information into the genomic DNA of infected cells via a reverse-transcribed DNA intermediate. This property of their life-cycle and the fact that parts of their genetic material can be replaced by foreign DNA sequences make retroviruses one of the most promising vectors for the delivery of genes in human gene therapy procedures, most notably for gene therapies which rely on gene transfer into dividing tissues. Most retroviral vector systems are based on mouse retroviruses and consist of two components, i.e., (i) the recombinant retroviral vector carrying the foreign sequences of interest, and (ii) so-called packaging cells expressing the structural viral proteins of which the encoding sequences are lacking in the retroviral vector. Expression of (i) in (ii) results in the production of recombinant retroviral particles capable of transducing susceptible target cells.

The infectivity and host cell range of the retrovirus particle is conferred by an envelope glycoprotein which specifically binds to a receptor molecule on the target cell membrane. The envelope glycoprotein of all known retroviruses consists of two associated peptides, which are derived by proteolytic cleavage from the same precursor protein encoded by the retroviral envelope (env) gene (Gunzburg and Salmons, 1996; Weiss, 1996). The amino terminal domain encompasses specific binding site(s) for its receptor on the target cell membrane determining the virus host range. Within this domain of about 200 amino acids, highly conserved sequences are present that are interrupted by two segments designated VRA and VRB which vary in sequence and length among various mammalian type C retroviruses (Battini et al., 1992). The carboxy terminal peptide, which contains trans-membrane anchor sequences, is assumed to account for the selective uptake of the envelope glycoprotein in the virus particle and to mediate fusion between the virus membrane and—depending on the type of virus—the plasma membrane or intracellular vesicle membrane of the target cell (Januszeski et al., 1997; Thomas et al., 1997). In FIG. 1 a schematic representation of the structure of MuLV env protein is given. Several envelope glycoprotein variants with different infection spectra for mammalian cells have been identified (Battini et al., 1992).

There are examples of recombinant viruses carrying an amphotropic or GaLV envelope. Recombinant viruses carrying an amphotropic or GaLV envelope are capable of infecting human and murine cells and are commonly used in gene transfer trials including human gene therapy involving the pluripotent hemopoietic stem cell (PHSC) (Havenga et al., 1997). Gene transfer frequencies into PHSCs of human patients and non-human primate animal models have been shown to be extremely low and limit therapeutic stem cell gene therapy (Havenga et al., 1997; Hoogerbrugge et al., 1996; Van Beusechem et al., 1993; van Beusechem et al., 1992).

One important limiting factor has been shown to be low expression levels of retroviral receptors such as the one mediating entry of amphotropic MuLV retrovirus (GLVR2) (Orlic et al., 1996; van Es et al., 1996). The quiescent state of PHSCs when isolated for ex vivo gene transfer procedures poses another blockade (Knaan-Shanzer et al., 1996). Murine stem cell gene therapy experiments have traditionally been performed with ecotropic MuLV vectors (Havenga et al., 1997). Recombinant viruses carrying an ecotropic envelope are only capable of infecting murine cells. Transfer of genes into murine PHSCs using ecotropic retroviral vectors has been shown to result in high transduction efficiencies in circulating PHSC derived peripheral blood cells (PBL). The transduction efficiencies are high enough to be therapeutic if achieved in human PHSCs reaching levels of PHSC gene transfer varying between 30–80%.

A small number of studies have been performed in which the transduction efficiency into murine PHSCs of ecotropic and amphotropic retroviruses were actually compared directly (Havenga et al., 1997). One of these studies indicated that infection with amphotropic retroviru's resulted in expression, and thus transgene presence for less than 8 weeks, whereas infection with ecotropic virus resulted in expression for more than 44 weeks after transplantation (Demarquoy, 1993). In a similar study, ecotropic virus was shown to be approximately 50 fold more efficient in transducing murine PHSCs as compared to amphotropic retrovirus (Orlic et al., 1996).

Ecotropic and amphotropic retrovirus differ in the receptor that is employed for virus entry (Albritton et al., 1989; van Zeijl et al., 1994). Ecotropic virus binds target cells via the ecotropic receptor mCAT1 which is a transporter of cationic L-amino acids (Kim et al., 1991) and amphotropic retrovirus binds target cells via the amphotropic receptor GLVR2, a sodium dependent phosphate transporter GLVR2 (Kavanaugh et al., 1994; Miller and Miller, 1994; van Zeijl et al., 1994).

A comparative study measuring mRNA levels of both the ecotropic and amphotropic receptors in mouse PHSCs (lin⁻c-kitbright) revealed an important difference. This study demonstrated that ecotropic receptor (mCAT1) mRNA levels in these cells are high, whereas amphotropic receptor (GLVR2) mRNA levels were undetectable by RT-PCR (Orlic et al., 1996). GLVR2 expression studies on CD34+ (CD38,CD33,CD71)⁻(CD34³⁰lin⁻ cells) isolated from human bone marrow, umbilical cord blood and immobilized peripheral blood supports these data (van Es et al., 1996).

Another important factor which plays a role in determining successful retroviral entry and integration is the post-binding route of entry of a retrovirus particle. The post-binding entry route for ecotropic virus is different from that of amphotropic retrovirus. Ecotropic retrovirus transductions are sensitive to lysosomotropic agents such as chloroquine and $NH_4Cl$. This suggests that upon binding of the ecotropic retrovirus, the retrovirus is internalized by receptor mediated endocytosis (McClure et al., 1990). In contrast, upon binding of the envelope of amphotropic retrovirus, the viral envelope directly fuses with the plasma membrane. This is a process that is not disrupted by lysosomotropic agents, suggesting that the post-binding steps of amphotropic MuLV virus are essentially different from those of ecotropic MuLV retrovirus (McClure et al., 1990).

The human homologue of the murine ecotropic virus receptor mCAT1 is hCAT1. Like mCAT1 mRNA expression in mouse PHSCs, hCAT1 mRNA is expressed at high levels in human PHSCs (Orlic et al., 1996). For both mCAT1 and hCAT1, the normal function is the import of cationic amino acids such as lysine and arginine (Albritton et al., 1993; Malhotra et al., 1996). The third predicted extracellular domain of mCAT1 includes a sequence YGE. The residues are crucial for receptor function. In the nonfunctional hCAT1, the sequence of the third extracellular domain is PGV. Mutation of the human sequence into one or two of the residues;, of mCAT1 results in an hCAT1 protein with ecotropic receptor function (Albritton et al., 1993; Yoshimoto et al., 1993). See, also, FIG. 2.

A number of mutant ecotropic envelope molecules have been described in the literature. MacKrell et al. have mutated amino acids within the receptor-binding domain VRA of ecotropic MuLV envelope in order to identify residues involved in receptor binding. Virions incorporating mutant envelopes carrying mutations at amino acid residue D84 have lost their binding capabilities to the ecotropic receptor mCAT1 (MacKrell et al., 1996). Virions carrying D84 mutated envelope protein were tested on human cells to search for a possible change in receptor recognition specificity but were found not to infect human cells (Mike Januszeski, personal communication).

Skov and Andersen have studied ecotropic Moloney envelope interactions with mCAT1 by generation of mutant envelope molecules with mutated arginine and lysine residues in gp70 including VRA followed by introduction in a replication competent retroviral backbone (Skov and Andersen, 1993). Mutations R135G, K137Q, R157G and R159A (R102G,K104Q,R124G and R126A without signal peptide respectively) resulted in virions that were not able to replicate.

Kingsman et al. have described in PCT International Patent application WO96/31602 an insertion site in the VRA domain of ecotropic envelope which allows modification of the tropism. An integrin binding sequence was inserted resulting in infection of human cells expressing the respective integrin.

PVC-211 murine leukemia virus (MuLV) is a neuropathogenic variant of ecotropic Friend MuLV (F-MuLV) that causes a rapidly progressive neurodegenerative disease in susceptible rodents. PVC-211 MuLV, but not the parental F-MuLV, can infect rat brain capillary endothelial cells (BCEC) efficiently, and the major determinant for BCEC tropism of PVC-211 MuLV is localized within the env gene. More specific analysis indicated that E116G and E129K substitutions in the background of the F-MuLV envelope protein were sufficient for conferring BCEC tropism on the virus (Masuda et al., 1996a). Host range changes of these mutations were found to include CHO cells normally not infectable with ecotropic F-MuLV or M-MuLV. The latter suggests that these mutations overcome a negative effect of CAT1 CHO cell receptor glycosylation in the region of virus binding in the third extracellular domain of mCAT1 (Masuda et al., 1996b).

By employing particular natural env variants, the transduction spectrum can be limited to some extent, but true specificity for human target cells of interest cannot be obtained following this strategy (Masuda et al., 1996a; von Kalle et al., 1994; Wilson et al., 1994).

In the present invention we describe the expansion of the host range of an ecotropic retrovirus or other gene transfer vehicle such as an adenoviral vector resulting in increased transduction of hemopoietic stem cells. In this invention, targeted delivery is accomplished by directing the retrovirus particle to cell membrane molecules differing from the natural receptor. This could then lead to increased specificity of transduction.

The present invention discloses examples of molecules that bind to hCAT1 and that can be used to develop gene transfer vehicles such as retroviral and adenoviral vectors. In particular, the invention relates to proteins and derivatives thereof expressed in the lipid bilayer of enveloped virus particles such as retroviruses. Methods, materials, procedures and pharmaceutical formulations for the design and preparation of the above molecules and virus particles are also part of the invention. These molecules and virus particles have applications in the field of virology, gene therapy, biochemistry and molecular biology.

The present invention relates to peptide molecules binding to hCAT1. These molecules are characterized by their ability to bind the third extracellular domain of the cationic amino acid transporter hCAT1 to either a synthetic peptide encompassing this third extracellular domain or by binding to cells expressing this domain of hCAT1 protein on their extracellular cell surface. These hCAT1 binding molecules can be peptides or antibody fragments displayed on a filamentous phage or as free molecules.

Included in the present invention are filamentous phages displaying hCAT1 binding molecules and that can be used to transfer genes into cells by modification of the phage genome using techniques known in the art.

Included in the present invention is the use of hCAT1 binding molecules to design vectors that employ hCAT1 to enter an HSC or any other cell expressing hCAT1. hCAT1 binding molecules can be incorporated in the envelope of a retrovirus or the capsid of any other viral or non-viral gene transfer vehicle such as an adenoviral vector. Incorporation of these hCAT1 binding sequences can be done using techniques known in the art.

Preferred are mutant retroviral envelopes that are derived from wild-type ecotropic envelope and which employ hCAT1 to enter the human or primate cell by binding to hCAT1. These new retroviral envelope molecules, when incorporated in a retroviral virion, will be able to infect hCAT1 positive cells such as human PHSCs at high efficiencies. The mutant retroviral envelopes can be used to pseudotype recombinant type C retrovirus including but not limited to murine leukemia retroviral vectors. In a further embodiment of the present invention, these hCAT1 binding envelopes can also be used to pseudotype lentiviral vectors including equine or HIV derived lentiviral vectors (Kim et al., 1998; Rizvi and Panganiban, 1992),(Kafri et al., 1997; Poeschla et al., 1996),(Miyoshi et al., 1997; Naldini et al., 1996b).

Figure 5:
FIG. 5 depicts a Northern blot analysis of cell lines with an hCAT1 probe.

Any hCAT1 binding envelope molecules or parts thereof made according to the methods described herein or other methods can be ligated into full length mammalian retroviral envelope expression constructs and introduced in cell lines expressing and containing all the sequences necessary for the generation of infectious and functional retroviral particles including but not limited to cell lines preferably derived from the adenoviral E1 transformed, human cell line PER.C6 (PCT Internet'l Patent Appl'n WO97/00326) and that express murine leukemia gag-pol constructs and a retroviral vector containing long terminal repeats (LTRs), and retroviral RNA packaging signals such as those vectors described in PCT Internet'l Patent Appl'n WO96/35798. The hCAT1 binding envelopes made according to the subject material of this invention can also be used to pseudotype vectors other than murine leukemia retroviral vectors including but not limited to lentiviral vectors (Naldini et al., 1996a; Naldini et al., 1996b).

In a further embodiment of the invention, hCAT1 binding sequences can also be incorporated in the capsid proteins of adenovirus including, but not limited to, the HI loop of the knob domain of an adenovirus (Krasnykh et al., 1998); preferably an adenovirus which does not bind to the adenoviral receptor CAR1 or MHC1. This results in an adenovirus that enters cells through hCAT1. Deduced from mCAT1 absent expression in mouse liver (Closs et al., 1993), an hCAT1 binding adenovirus does not exhibit liver transduction when administered in vivo. By combining an hCAT1 targeted knob with a ligand for another in vivo target hCAT1 targeting of an adenovirus can remove an important limitation of in vivo use of adenoviral vectors for gene therapy (Sullivan et al., 1997). In another embodiment, an hCAT1 targeted adenovirus will more efficiently transduce cells that are difficult to transduce such as endothelial cells or smooth muscle cells as compared to a wild-type adenoviral vector including but not limited to an adenoviral vector derived from the adenoviral serotype 5.

An hCAT1 targeted adenovirus is useful for local applications of adenoviral vector such as in patients with restenosis following balloon angioplasty where smooth muscle cells need to be transduced with, for example, an adenoviral vector carrying the ceNOS cDNA. More efficient transduction of these tissues results in lower multiplicities of infections (MOIs) that can be used and therefore less vector associated toxicity to the tissues surrounding the target cells (PCT Internet'l Patent Appl'n PCT/EP98/00723).

In another aspect of the present invention, the hCAT1 binding human FAbs that are part of the subject matter of this invention can be used to measure expression of hCAT1 molecules on cells that are targets for gene therapy using hCAT1 mediated gene transfer including but not limited to mammalian hemopoietic stem cells such as CD34+CD38− or CD34+(CD33CD38CD71)− cells. This could be part of a procedure aimed at determining when or whether a patients cells are most susceptible to gene transfer through hCAT1 including but not limited to adenoviral or retroviral gene transfer vehicles.

The skilled artisan will be able to apply the teaching of the present invention to other virus capsid or envelope or non-viral gene transfer molecules or vehicles than those exemplified herein without departing from the present invention and therefore the examples presented are illustrations and not limitations. It is intended that all such other examples be included within the scope of the appended claims.

EXAMPLES

Example 1

Sequences of hCAT1 cDNAs Amplified from Human CD34+ Cells

For the purpose of developing gene transfer tools that enter PHSCs through hCAT1, specifically through binding to the third extracellular domain, we isolated total RNA from a number of different human $CD34^+$ samples and determined the cDNA sequence of hCAT1 (see, FIG. 2). Total RNA was isolated according to the protocol described by Chomczynski et al. (Chomczynski and Sacchi, 1987). RT-PCR was performed by using the SuperScript Preamplification System for First Strand cDNA Synthesis (Life Technologies). For first strand synthesis random hexamers were used. The hCAT1 cDNA was amplified with two sets of primers, each resulting in a product of approximately 1 kb encompassing the open reading frame of the hCAT1 mRNA (Yoshimoto et al., 1991). DNA sequencing was performed by BaseClear, Leiden, The Netherlands, using automated sequence analysis. In FIGS. 3*a* and 3*b*, the results of sequence analysis of hCAT1 cDNA isolated from $CD34^+$ cells from mobilized peripheral blood or umbilical cord blood are compiled. Clearly from these nucleotide sequence analyses (FIG. 3*b*) it can be deduced that indeed in the $CD34^+$ samples tested, hCAT1 is expressed and includes the third extracellular domain with predicted sequence KNWQLTEEDFGNTSGRLCLNNDTKEGKPGVGGF (SEQ. ID. NO. 2) which includes the sequence PGV determining function as receptor (see, above). Therefore, targeting through this domain or part of this domain of hCAT1 in hemopoietic $CD34^+$ cells including but not limited to hemopoietic stem cells such as defined by lineage negative phenotypes, e.g.,$CD34^+CD38^-$, is possible.

Example 2

Peptide Phage Display to Select hCAT1 Binding Peptides

To isolate peptides that bind to the third extracellular domain of hCAT1 (Albritton et al., 1993)(FIG. 2) we employed peptide phage display. A 12 mer peptide phage display library was purchased from New England Biolabs. This library is constructed in the filamentous *E. coli* phage m13 and the peptide sequences are displayed as N-terminal fusion proteins with the minor coat protein pIII. The unamplified library had a complexity of $1.9\times10^9$ different sequences as determined by the suppliers. We amplified the library once before using it to select hCAT1 binding peptide phages. Two targets were used to select for peptide displaying phages which bind to the third extracellular domain of hCAT1. First, the predicted third extracellular domain of hCAT1 was synthesized as a synthetic peptide by Neosystem, Strasbourg, France. The N-terminus of this peptide was biotinylated and followed by three amino acid linker residues KRR, followed by the predicted sequence of the third extracellular domain (FIG. 4). Second, we generated cell lines derived from the human 911 cell line that overexpress hCAT1 as judged by steady-state mRNA expression levels. The hCAT1 expression construct hATRCC1, which is a pcDNA3 based expression construct of the hCAT1 cDNA (Malhotra et al., 1996), was employed to transfect 911 cell lines followed by selection for neomycine resistance in 1 mg/ml of G418 (Genetecin, Life Technologies, Inc). A cloned cell line designated k08 was isolated which expresses high levels of hATRCC1 derived hCAT1 mRNA (FIG. 5).

To select for peptide displaying phages that bind to the putative third extracellular domain of hCAT1 as expressed on human cells, the following selection procedure was employed. Six rounds of selection on biotinylated hCAT1 peptide (FIG. 4) followed by three rounds of selection on hCAT1 overexpressing cells k08. Initially, two separate selections were carried out differing in the stringency of washing. Low stringency washing consisted of 3 washes with 2% (w/v) milk powder in PBS with 0.05% (v/v) Tween 20 and 3 washes with PBS. High stringency washing consisted of 5 washes with 2% (w/v) milk powder, PBS with 0.05% Tween 20, 5 washes with PBS, 0.05% Tween 20 and 5 washes with PBS. After 1 round of selection on 911-hCAT1-k08 cells, eluted phages from both washing procedures were pooled and used for a second and third round of selection on 911-hCAT1-k08 cells. The results of these experiments are depicted in Table 1. Clearly the ratio of input over output increases upon selection on hCAT1 peptide indicative of selection for binding phages. When selection on hCAT1 positive cells was started, the ratio drops and slightly increases in the last round on hCAT1 expressing human cells.

Figure 6:
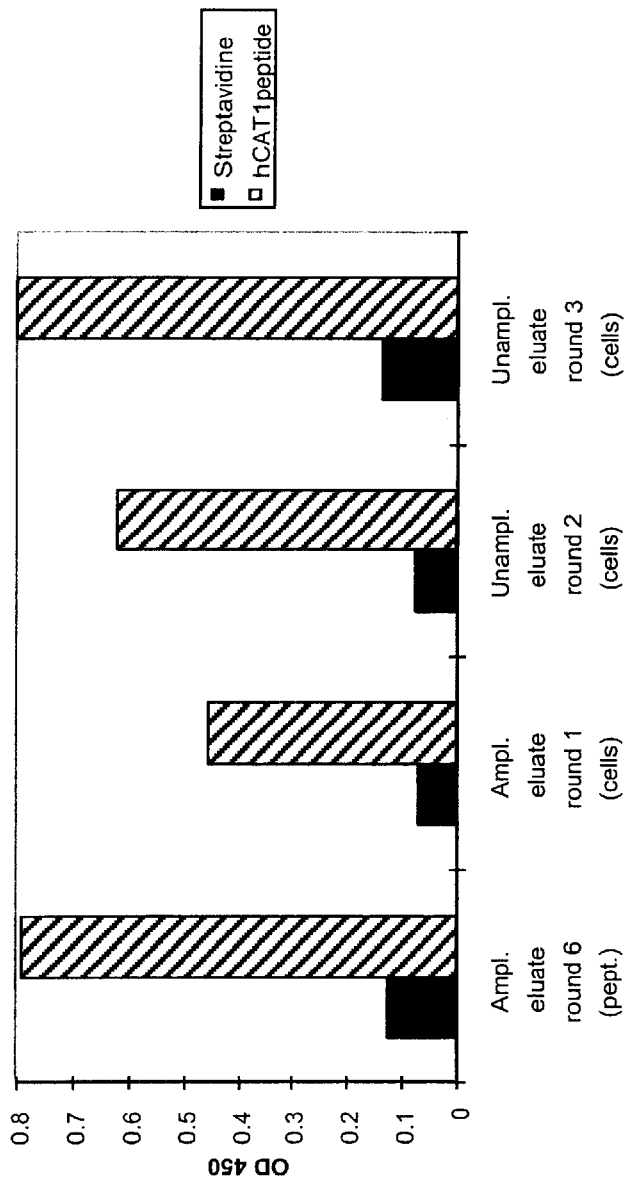
FIG. 6 is a bar graph depicting the results of an ELISA with 12-mer peptide phages as described herein.
Figure 7:
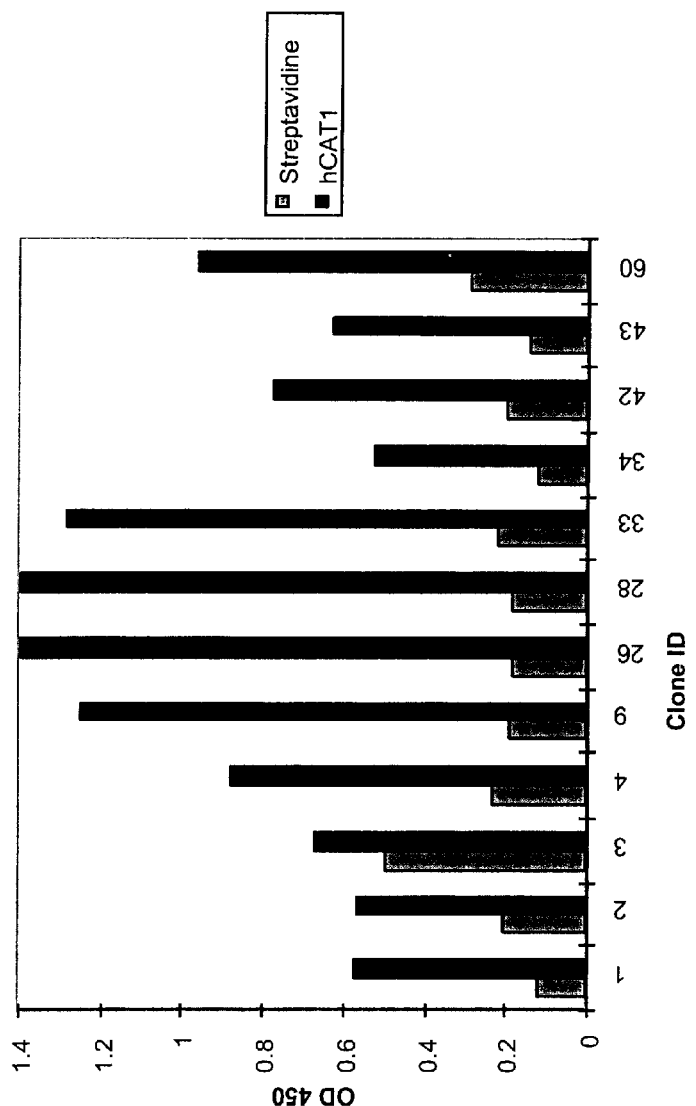
FIG. 7 is a bar graph depicting the binding of cloned 12 mer peptide displaying phages to hCAT1 peptide as measured by ELISA.

After the last round of selection with the hCAT1 peptide and after each round of cell selection, the pools of peptide displaying phages were tested for binding to immobilized hCAT1 peptide using an Enzyme Linked Immunosorbent Assay ("ELISA" or "EIA"). 96-well plates were coated with 2 mg/ml biotinylated BSA in PBS and incubated for 1 hour 37° C. after which the wells were rinsed 3× for 5 minutes with PBS/0.05% Tween 20. Then the wells were saturated with streptavidin (10 mg/ml in PBS/0.5% gelatin) for 1 hour at room temperature (RT) and washed 3 times with PBS/0.05% Tween 20. Then the wells were incubated overnight at 4° C. with biotinylated hCAT1 peptide (FIG. 4) at a concentration of 10 mg/ml in PBS. The next day the wells were rinsed two times with PBS/0.1% Tween 20 and 2× with PBS. Then the wells were blocked with 2% non-fat milkpowder in PBS for at least 30 minutes at RT followed by three rinses with with PBS/0.1% Tween and three with PBS. Subsequently, an equal volume of 4% non-fat milkpowder in PBS was added to all wells and culture supernatant or purified phage (PEG precipitated) and incubated for 1.5 hours at RT. After this incubation, the wells were washed three times with PBS/0.1% Tween 20 and three times with PBS followed by incubation with an anti-m13 antibody solution (Pharmacia, 1:5000 in 2% non-fat milkpowder in PBS) for 1 hour at RT. Again the wells were washed three times with PBS/0.1% Tween and three times with PBS followed by the addition of a rabbit-anti goat HRP conjugate solution (BioRad, 1:2000 in 2% non-fat milkpowder in PBS) for 1 hour at RT. After this incubation, the wells were washed again three times with PBS/0.1% Tween and three times with PBS. Detection of phage binding was then visualized using TMB colour solution (0.1 mg/ml TMB, 1% DMSO, 1× TMB buffer, 0.001% 30% $H_2O_2$ in $H_2O$) 20–30 min in the dark at RT and stopped with 2 N $H_2SO_4$ and read at 450 nm in a microplate reader. Using this hCAT1-specific. ELISA, an enrichment of phages binding to hCAT1 peptide is achieved (FIG. 6). Importantly, after binding of the peptide selected pools to hCAT1 overexpressing cells, eluted phages still bind to hCAT1 peptide. Clones isolated from round 3 on hCAT1 overexpressing cells were isolated and tested on hCAT1 peptide ELISA (FIG. 7). Except 1, all tested clones bound to hCAT1 peptide and thus to the third extracellular domain displayed on human cells.

To confirm enrichment for specific sequences and to determine the amino acid sequence of the 12 mer peptides displayed, we isolated single stranded m13 phage DNA for automated sequence analysis (Baseclear, Leiden, The Netherlands). The oligonucleotide used for sequencing was 5'-CCCTCATAGTTAGCGTAACG-3' (SEQ. ID. NO. 3). We sequenced clones isolated from the pools of various peptide and cell selections. For this purpose we pooled the eluates of the two different washing conditions. In addition to the amplified 12 mer peptide library, we only selected clones from peptide rounds 3,5 and 6 and cell rounds 1,2 and 3. In Table 2, the sequences determined for the various clones are given. Clearly, a very strong selection occurred because all cell selected phage clones displayed one sequence namely: SVSVGMKPSPRP (SEQ. ID. NO. 1). This sequence is also displayed by phages in hCAT1 peptide selected pool 6 in a mixture with 3 other sequences. These other phages are lost once the phage pools selected on hCAT1 peptide are selected for binding to hCAT1 overexpressing cells.

Figure 8:
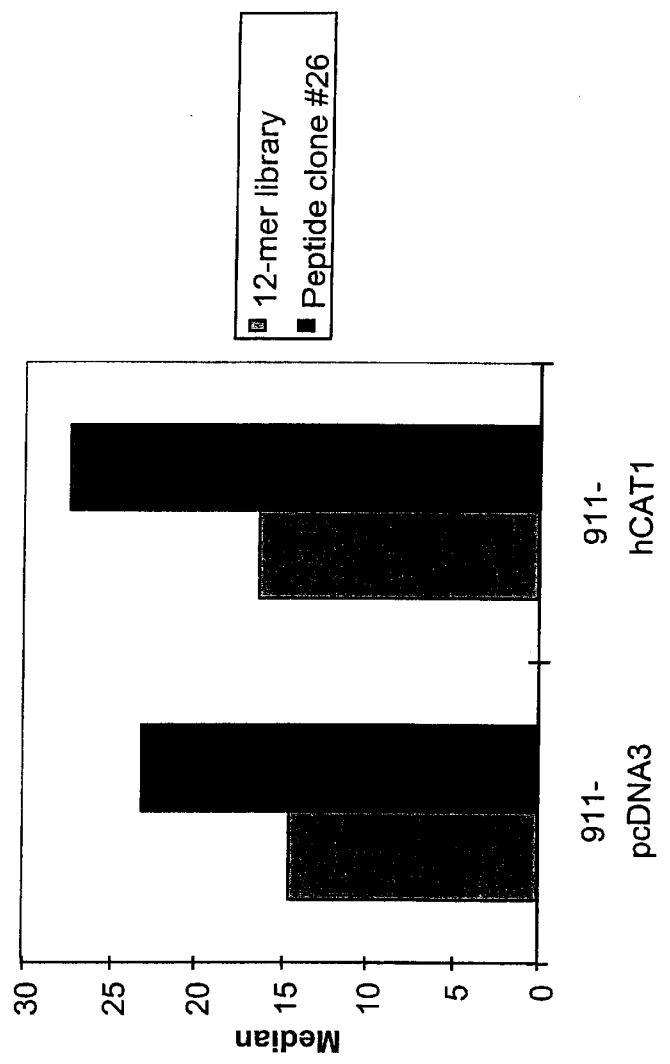
FIG. 8 is a bar graph depicting the binding of a particular peptide (SEQ. ID. NO. 1) displaying phage measured by flow cytometry.

The cloned SVSVGMKPSPRP (SEQ. ID. NO. 1) displaying m13 phage was used in experiments to measure binding of the displayed sequence to cells that express hCAT1. First, we did an experiment using the flow cytometer and the 2 cell lines 911-pcDNA3 and 911-hCAT1(k08).Cells were incubated with $10^{11}$ phage in 100 ml PBS/0.1% BSA for 1 hour at room temperature. Subsequently, the cells were washed twice with PBS/0.1% BSA followed by incubation of the cells with anti-m13 antibody (Pharmacia, 1:500 in PBS/0.1% BSA) for 30 min at room temperature and washed twice with PBS/0.1% BSA. Then the cells were incubated with rabbit-anti goat FITC (DAKO, 1:50 in PBS/0.1% BSA) for 30 min at RT and washed twice with PBS/0.1% BSA. Binding of phage was then measured in the FL1 channel of a Becton and Dickinson flow cytometer. As a control, we used an identical amount of phage from the amplified 12 mer library. In FIG. 8, the results of this experiment are depicted. Clone #26 phage binds to 911 cells and in particular to 911 cells that over-express hCAT1.

We also measured cell binding of phage incubating hCAT1 expressing cells with phage followed by titering total cell bound phage, eluted phage and cell associated phage fractions on E. coli using a standard m13 plating assay on a lawn of E. coli cells. For this purpose, E. coli strain ER2537 is grown overnight in LB medium. This overnight culture is then used to inoculate 20 ml of fresh LB medium at an $OD_{600nm}$ of 0.05. Once at an $OD_{600nm}$ of 0.5, 500 ml of the ER2537 E. coli bacteria were mixed with 500 ml dilutions of phage samples and incubated at RT for 10 min. Plating on a standard LB-agar plate was performed by mixing 3 ml top agar with 200 ml of each sample. Once the top agar was solidified, the plates were transferred upside down to a 37° C. incubator for 12–14 hours. Plaques were counted and used to determine the number of phage particles binding to hCAT1 expressing cells. In Table 3 cell binding is depicted.

Clearly, from these results we can conclude that the 12 mer peptide displaying phage with sequence SVSVGMKPSPRP(SEQ. ID. NO. 1) indeed binds to hCAT1 expressing cells. hCAT1 expressing cells were also incubated at 37° C., followed by elution of bound phages plus cell associated phages were liberated. Both were used in phage titering on E. coli and clearly a cell associated fraction is detected. This suggests that the phage displaying sequence SVSVGMKPSPRP (SEQ. ID. NO. 1) and which bind to hCAT1 also enter a human hCAT1 expressing cell. This feature of sequence SVSVGMKPSPRP(SEQ. ID. NO. 1) could be used for the development of gene transfer products useful in gene therapy.

Figure 2:
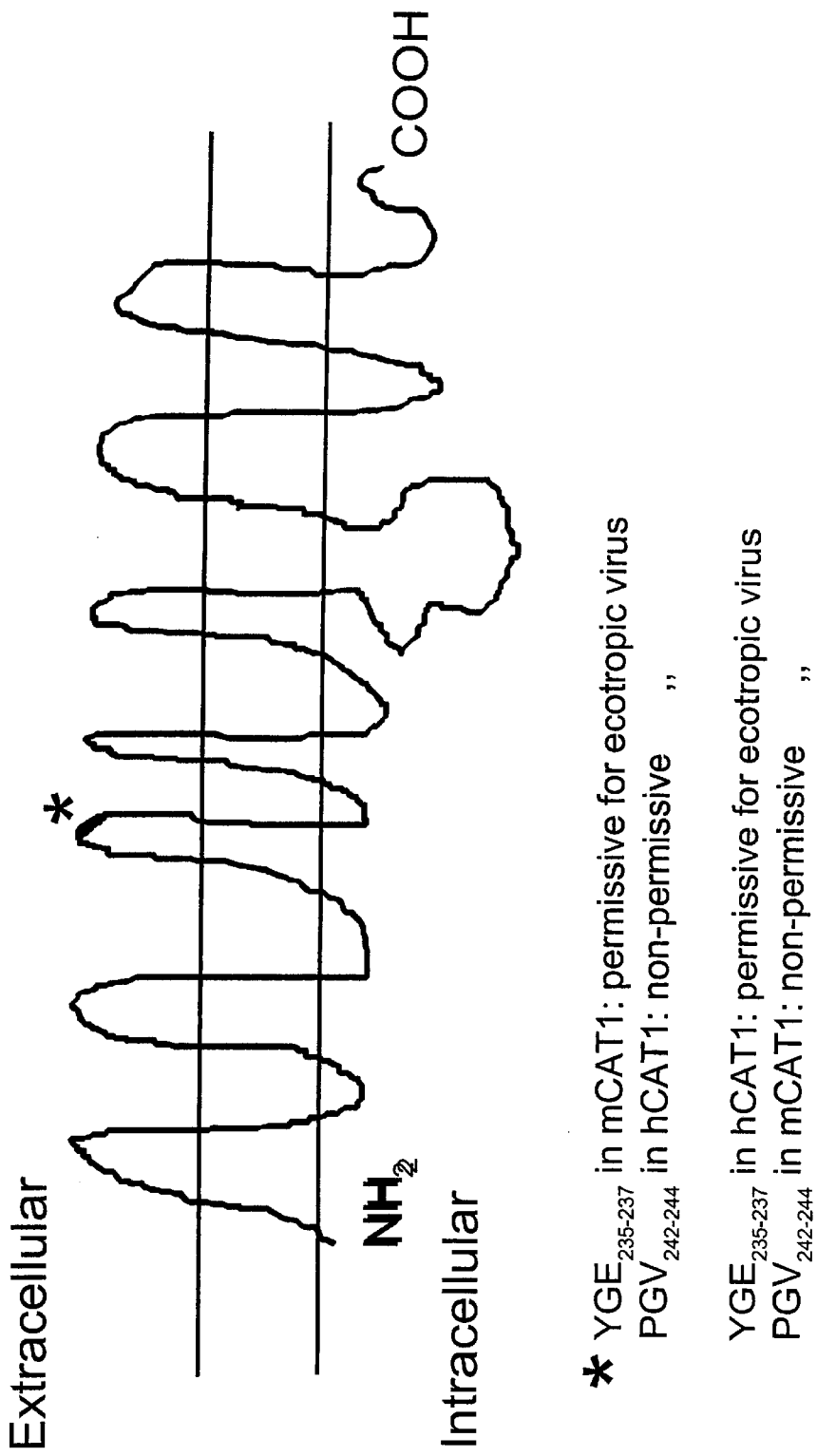
FIG. 2 graphically depicts the theoretical topology of CAT-1 receptors in plasma membrane (extracellular).
Figure 3:
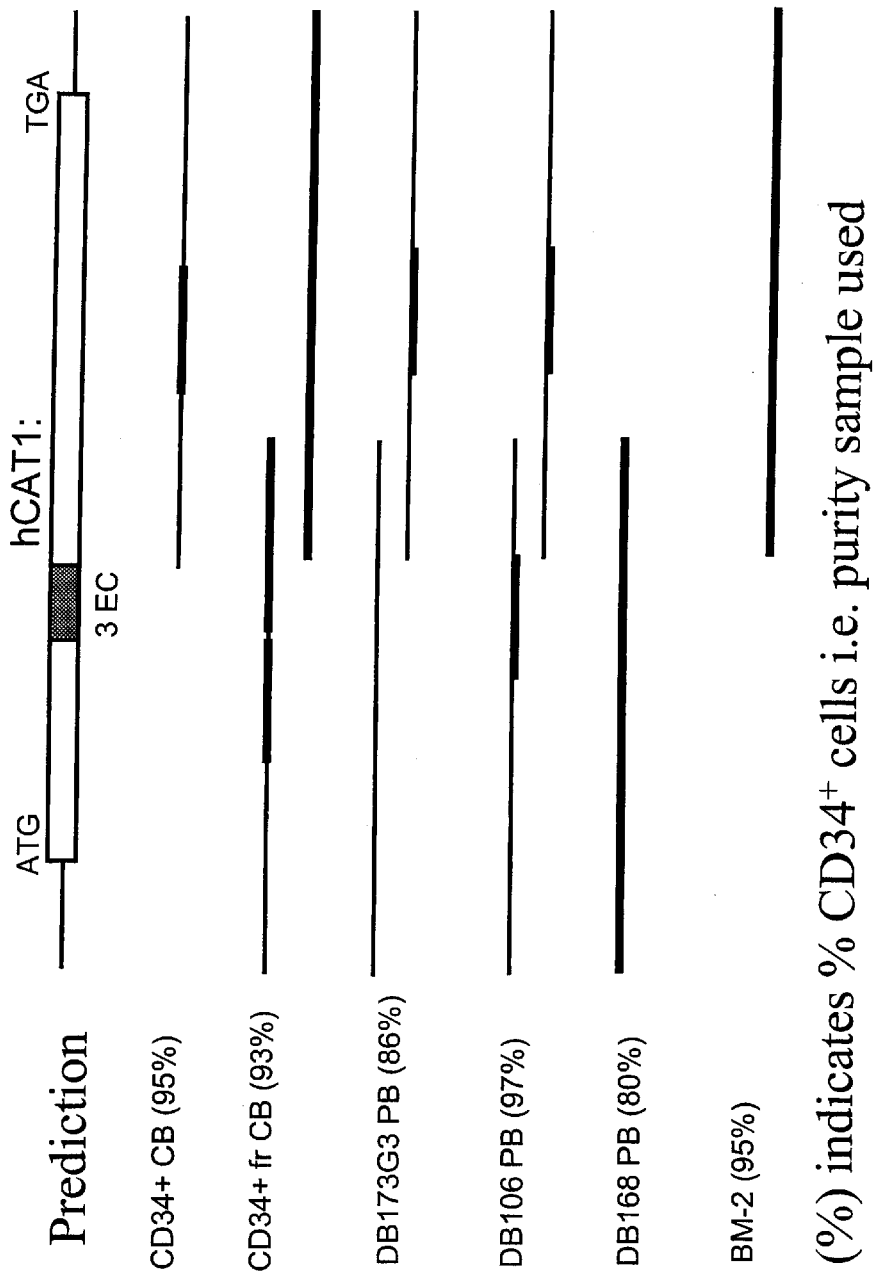
FIG. 3a graphically depicts the sequencing of hCAT1 cDNA isolated from human CD34+ hematopoietic cells.
FIG. 3b depicts the sequencing of third extracellular domain hCAT1 cDNA isolated from human CD34+ hematopoietic cells (SEQ. ID. NO. 73 and 74).
Figure 4:
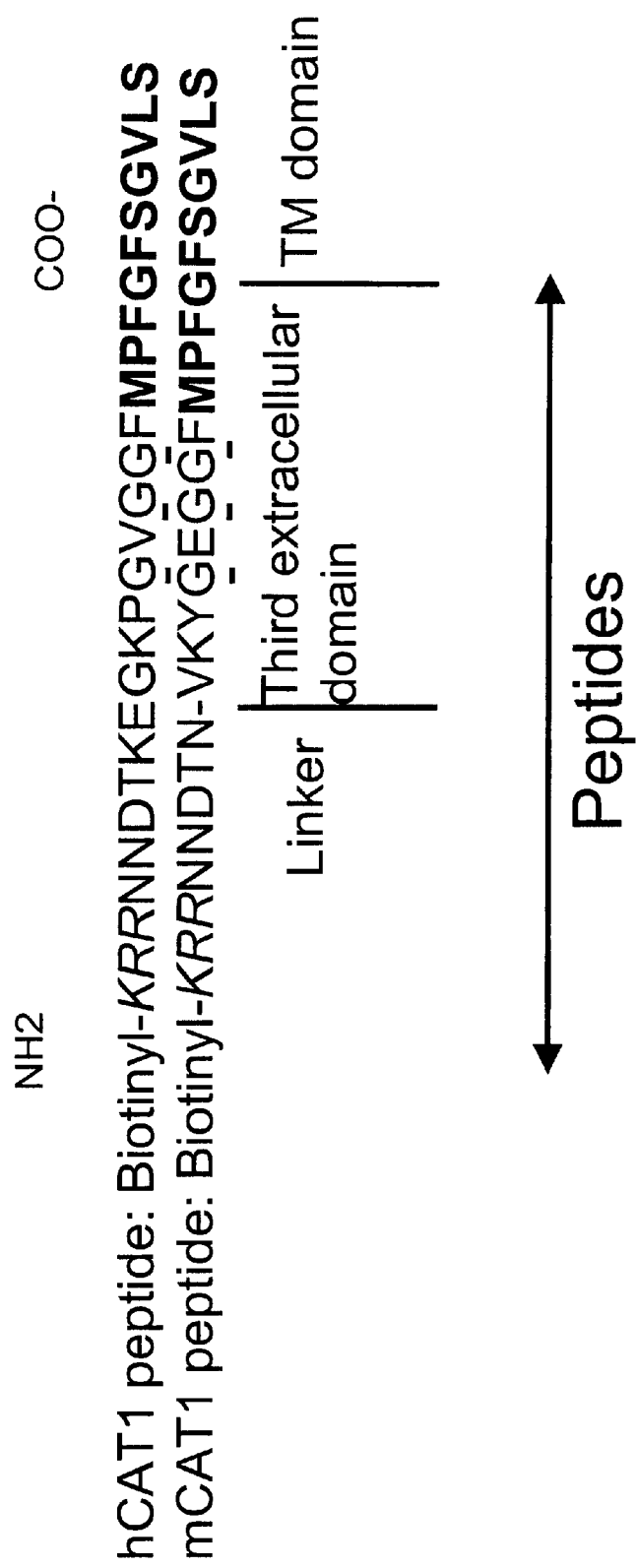
FIG. 4 depicts synthetic sequence hCAT1 and mCAT1 peptides (SEQ. ID. NO. 75 and 76).

Example 3
Human FAb Phage Display to Select hCAT1 Binding Human Antibody Molecules To isolate antibodies that bind to the third extracellular domain of hCAT1 (Albritton et al., 1993) (FIGS. 2 & 4), we employed phages displaying human FAb fragments encompassing the light and heavy variable and constant regions. A human FAb phage display library was constructed in phage display vector pCES1, a vector derived from pCANTAB6 (McGuiness et al., 1996). The library was constructed in the filamentous E. coli phage m13 and the FAb sequences are displayed partly as N-terminal fusion proteins with the minor coat protein pIII. The unamplified library had a complexity of approximately $3.3 \times 10^{10}$ different sequences. Two targets were used to select for peptide displaying phages which bind to the third extracellular domain of hCAT1. First, the predicted third extracellular domain of hCAT1 was synthesized as a synthetic peptide by Neosystem, Strasbourg, France. The N-terminus of this peptide was biotinylated and followed by three amino acid linker residues KRR, followed by the predicted sequence of the third extracellular domain (FIGS. 2 & 4). Second, we generated cell lines derived from the human 911 cell line that over-express hCAT1 as judged by steady-state mRNA expression levels. The hCAT1 expression construct hATRCC1, which is a pcDNA3 based expression construct of the hCAT1 cDNA, was employed to transfect 911 cell lines followed by selection for neomycin resistance in 1 mg/ml of G418 (Geneticin, Life Technologies, Inc). A cloned cell line designated k08 was isolated which expresses high levels of hATRCC1 derived hCAT1 mRNA (FIG. 5).

To select for FAb displaying phages that bind to the putative third extracellular domain of hCAT1 as expressed on human cells, the following selection procedure was employed: four rounds of selection on biotinylated hCAT1 peptide (FIG. 4) followed by three rounds of selection on hCAT1 overexpressing cells k08. For selection on biotinylated hCAT1 peptide, 250 ml of FAb library (or eluted phage from the previous round) was mixed with 250 ml 4% Marvel in PBS and equilibrated while rotating at RT for 1 hour. Subsequently, biotinylated hCAT1 peptide (20–500 nM in $H_2O$) was added. This mix was incubated on the rotator at RT for 1 hour before 250 ml equilibrated streptavidin-dynabeads in 2% Marvel in PBS was added. After incubation on a rotator at RT for 15 min, the beads with the bound phage were washed 5 times with PBS/2% Marvel/0.1% Tween, 5 times with PBS /0.1% Tween and 5 times with PBS. Then the phage were eluted by incubation with 0.1M Tri-ethyl-amine on a rotator at RT for 10 min and neutralized in 1 M Tris-HCl pH 7.4. The eluted phage were titered and amplified in TG1 before the next selection. For selection on 911-hCAT1 cells, the cells were harvested at a confluency of about 80% and suspended in PBS/10% FBS/2% Marvel to a final concentration of at least $3 \times 10^6$ cells/ml. This cell suspension was incubated for 30 min on a rowing boat mixer (or rotator), while at the same time, phage were also pre-incubated in PBS/10% FBS/2% Marvel. Then the cells were centrifuged, resuspended in the pre-incubated phage solution and incubated on a rowing boat mixer (or rotator) for 1 hour. Afterwards, the cells were washed 10 times with PBS/10% FBS/2% Marvel and twice with PBS. The cells were centrifuged and resuspended in 0.6 ml water. Subsequently, 0.6 ml 200 mM triethylamine was added (drop-wise while vortexing). After 5 minutes, the suspension was neutralized by adding 0.6 ml of 1 M Tris-HCl pH 7.4 (drop-wise while vortexing). After centrifugation (5 min, 14000 rpm), the supernatant was transferred to a new tube and titered and amplified in TG1 before the next selection. The results of these experiments are depicted in Table 4. Clearly, the ratio of input over output increases upon selection on hCAT1 peptide indicative of selection for hCAT1 peptide binding phages. When selection on hCAT1 positive cells was started, the ratio dropped and slightly increased in the last round on hCAT1 expressing cells.

Figure 9:
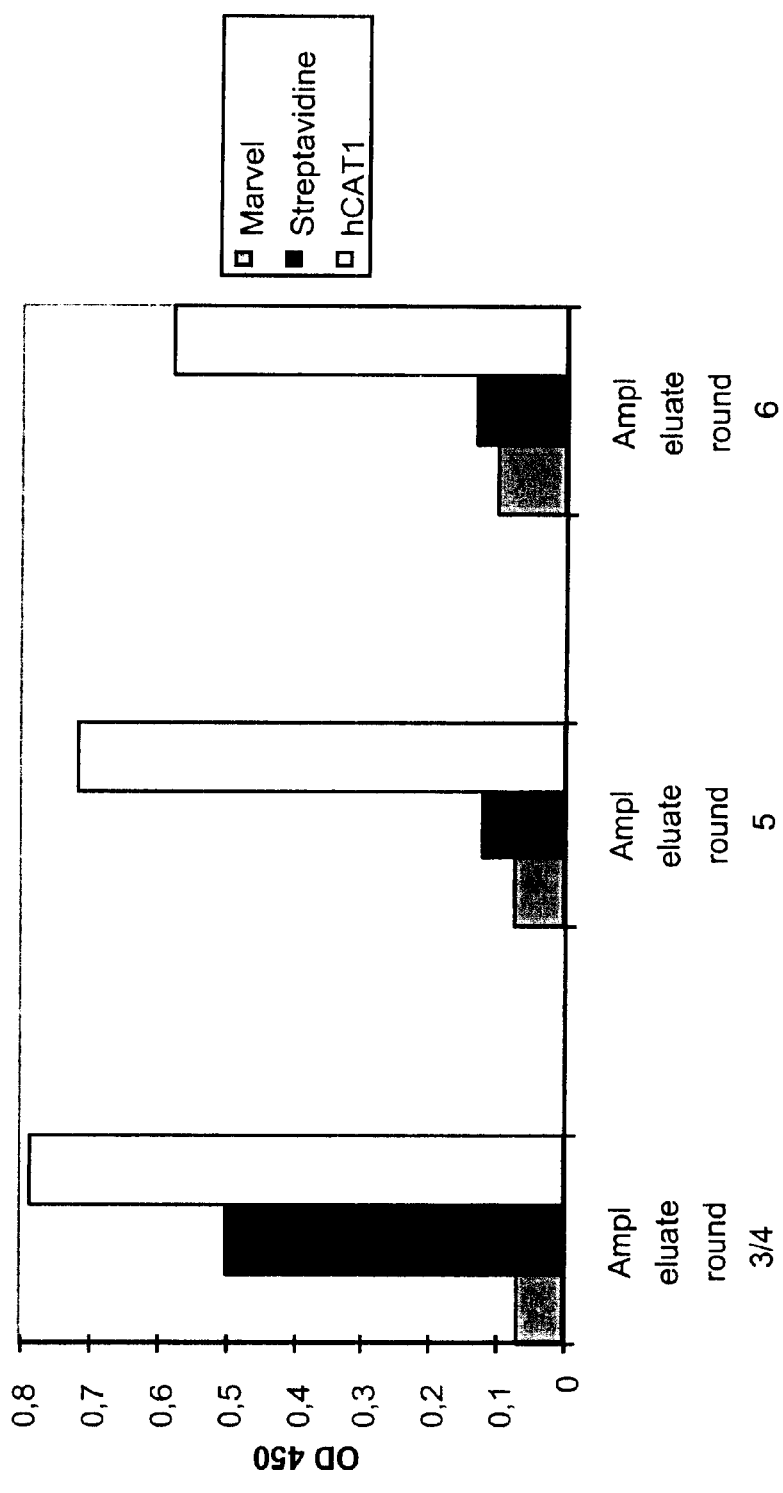
FIG. 9 is a bar graph depicting the results of ELISA with pools of human Fab phages.
Figure 10:
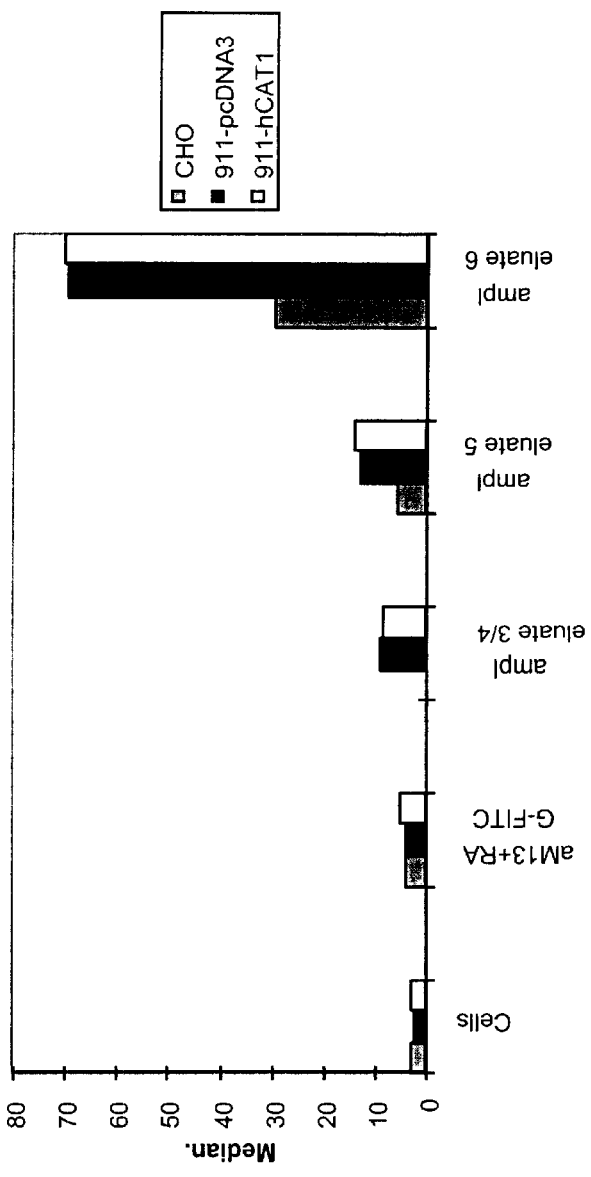
FIG. 10 is a bar graph depicting the binding of human FAb displaying phage pools measured by flow cytometry.
Figure 11:
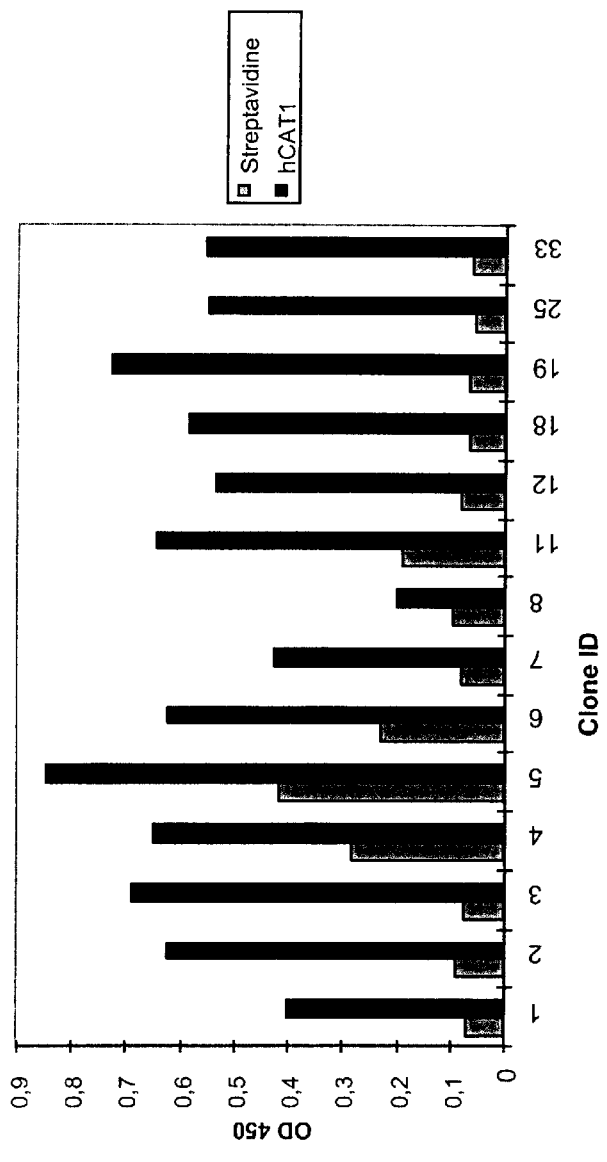
FIG. 11 is a bar graph depicting the binding of cloned human FAb displaying phages to hCAT1 peptide as measured by ELISA.
Figure 13:
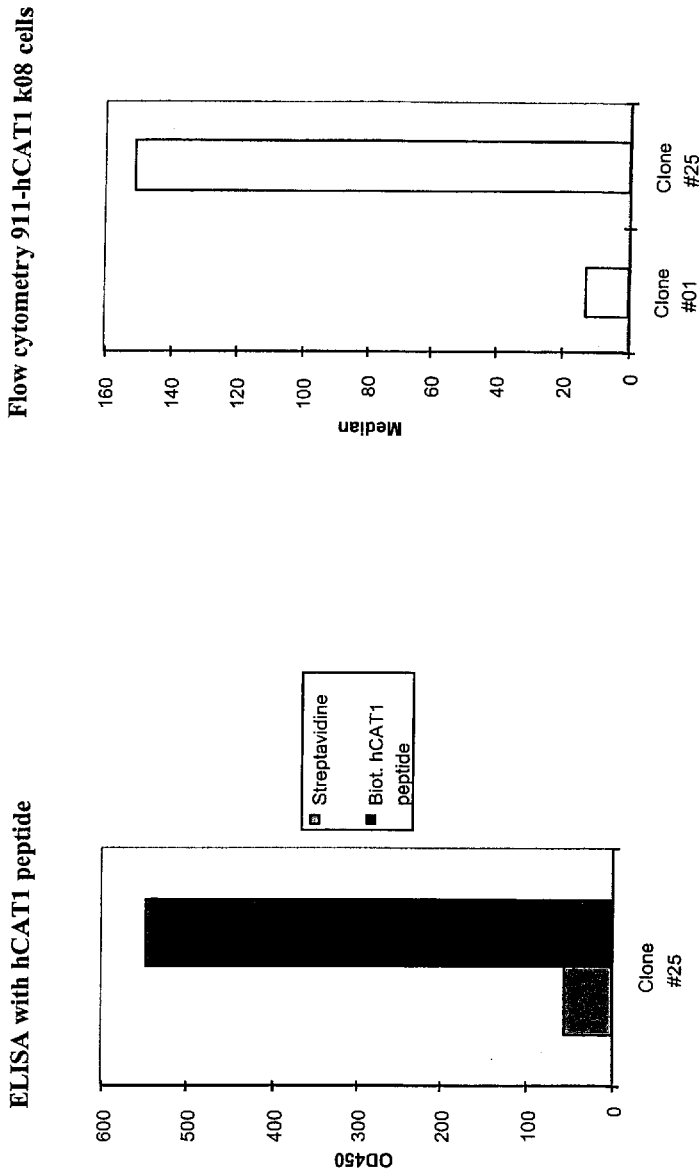
FIG. 13 depicts two bar graphs depicting the performance of example FAb phage clone #25 binding to hCAT1 peptide and hCAT1 expressing unfixed cells as described herein.
Figure 14:
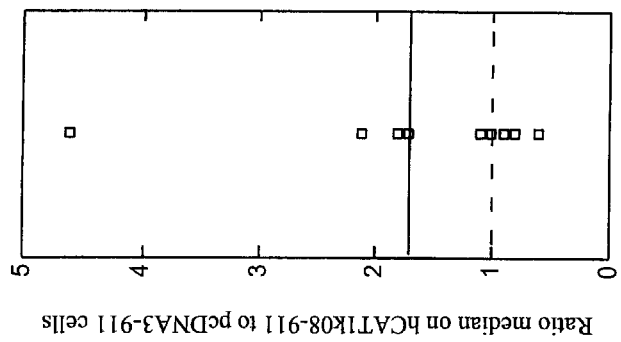
FIG. 14 depicts the binding of FAb phage clone #25 to hCAT1 overexpressing cells.
Figure 15:
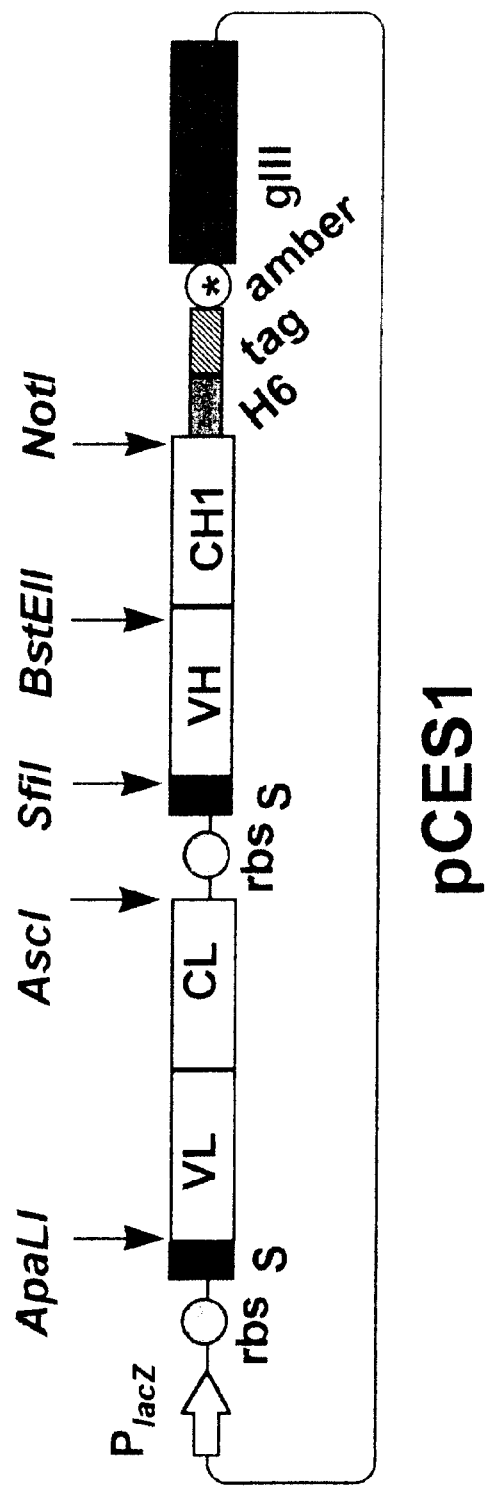
FIG. 15 graphically depicts vector pCES1 used for construction of a human FAb display library.
Figure 17:
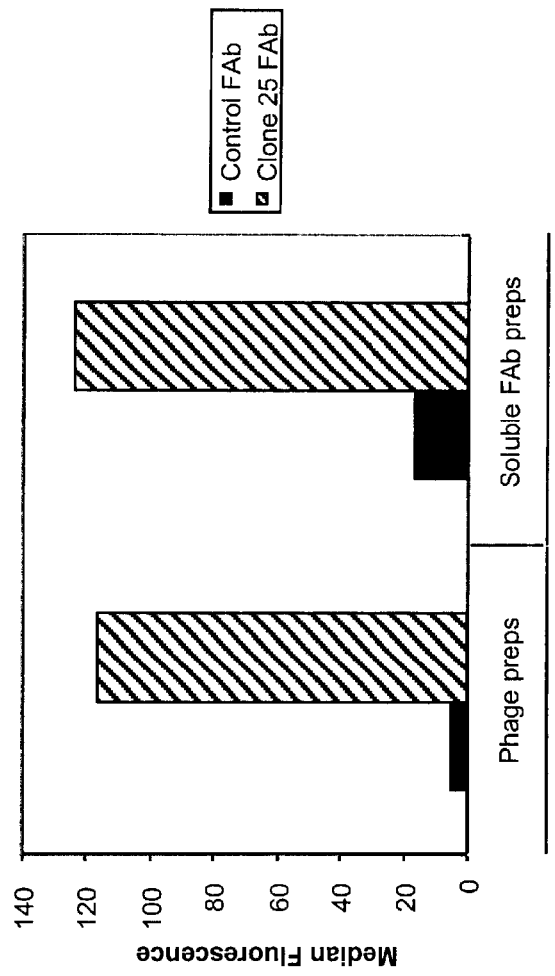
FIG. 17 is a bar graph depicting the binding of soluble FAb fragments to hCAT1 expressing cells.

The pools of the last 3 rounds were tested for binding to the biotinylated hCAT1 peptide in an hCAT1-specific ELISA and also for cell binding by flow cytometric analysis (both protocols are described in Example 2). After the last round of selection on cells, the pool of FAb phages still binds to the biotinylated hCAT1 peptide (FIG. 9). Flow cytometric analysis showed that this pool also binds to hCAT1 over-expressing cells (FIG. 10). From this pool, 43 clones were analyzed by fingerprint analysis and divided into 14 different groups. From each group, 1 phage clone was tested for binding to the biotinylated hCAT1 peptide in an hCAT1-specific ELISA and also for cell binding by FACS analysis. Three clones appeared to be streptavidin binders, whereas the other 11 clones showed binding to the biotinylated hCAT1 peptide (FIG. 11). Flow cytometric analysis revealed that only 1 of the 14 clones showed strong binding to hCAT1 overexpressing cells (FIG. 12). This clone was analyzed in more detail (FIGS. 13 & 14). Clearly, clone #25 binds strongly to the synthetic hCAT1 peptide used and to hCAT1 overexpressing 911 k08 cells. Moreover, average fold increased binding of this phage to 911-hCAT1-k08 overexpressing cells over 911-pcDNA3 cells was found to be 1.6±1.2 fold (FIG. 14). Double strand phagemid DNA was prepared and used to determine the nucleotide and deduced amino acid sequence of the displayed variable heavy and light chains. For a schematic picture of the vector pCES1 in which the library of variable chains was cloned see FIG. 15. The hCAT1 binding domains are, as expected, homologous to human immunoglobulin sequences. The complementarity determining regions (CDRs) are indicated in FIG. 16.

The sequences of this immunoglobulin can be incorporated in viral or non-viral proteins that mediate binding and entry to cells and thus create gene transfer vehicles that enter cells through hCAT1. The hCAT1 binding human FAbs can also be used to measure expression of hCAT1 on cells that are targets for gene therapy using hCAT1 mediated gene transfer.

Example 4
Incorporation of hCAT1 Binding Peptides in Ecotropic Retroviral Envelope To include hCAT1 binding peptides (see, Example 2) in the context of an ecotropic murine leukemia viral envelope, we used functional display of ecotropic envelope by filamentous phages. We used the construct gpIII/env2 which encodes a fusion protein consisting of a prokaryotic signal peptide and all of the gp70 protein including the variable regions A and B and the polyproline hinge(amino acid residues 34–308) fused to the capsid protein encoded by gene III of m13. Numbering of amino acid sequences was done according to the unprocessed envelope: sequence as deposited in the Swiss prot database with accession number P03385 and starting from the viral signal peptide. In Table 5, all the oligonucleotides are depicted that are used for insertion of the peptide sequences in the retroviral envelope.

Three sites and ways of peptide insertion have been chosen: (1) Insertion at the BstEII site of the ecotropic envelope; (2) Replacement of sequence PFSS (residues 96–99) by each of the 4 peptides (see, Table 5); and (3) Replacement of sequence LTSLTP (residues 122–127) by each of the 4 peptide sequences (see, Table 5). The sequences PFSS and LTSLTP are predicted to be displayed on the outside of the envelope protein as deduced from the structure of crystallized Friend ecotropic envelope (Fass et al., 1997). For the BstEII insertion constructs, the two single stranded complementary oligonucleotides were synthesized. At the amino acid sequence level, linker amino acids were included at the amino and carboxy terminus of the inserted peptide sequence. These single stranded oligonucleotides were then mixed in equimolar fashion, heated to 95° C. and slowly cooled to room temperature to allow hybridization of the complementary molecules to double stranded DNA. Annealing was followed by BstEII digestion and separation on a 2% agarose gel run in TAE-buffer. DNA was then excised from the gel and purified using Qiaquick gel extraction kit (Qiagen, Germany). At the same time, double stranded phagemid DNA of construct gpIII/env2 was digested and thus linearized with BstEII. Linearized gpIII/env2 DNA was subjected to an incubation with the thermosensitive alkaline phosphatase TSAP (Life technologies), then mixed in various molar ratios with double stranded BstEII digested oligonucleotides encoding any of the 4 hCAT1 binding peptides (see, Table 5b). Then 1 unit of T4 ligase and T4 ligase buffer supplemented with 1 mM ATP was added. The ligation mixture was incubated for 1 hour at +20° C. The ligation mixtures were then transformed into Max DH5a competent bacteria (Life Technologies). Ampicillin resistant colonies were picked and subjected to a PCR with one of the 4 primers in Table 5c and primer Ecoenv12 (see, Table 5). This PCR allows one to determine the nature of the inserted sequence and its orientation. Plasmid DNA of colonies with correct orientation of insert DNA was then isolated using Qiagen columns and sequenced (Baseclear, Leiden) to confirm the complete sequence of the inserts and boundaries plus their orientation.

For the insertion/deletion of hCAT1 binding peptide sequences into gpIII/env2 at the LTSLTP and PFSS positions, two fragments were amplified (primary PCR) using Elongase polymerase and the following two pairs of primers: Fragment 1: Ecoenv17 (sense primer, Table 5c) plus one of the even numbered oligonucleotides in Table 5a. Fragment 2: Ecoenv12 or ecoenv05 (antisense, Table 5c) plus an odd numbered primer in Table 5a. Fragment 1 harbors at the DNA level the 3' end, whereas fragment 2 harbors the peptide insertion at the 5' end. Because both fragments have identical 3' (fragment 1) and 5' ends (fragment 2), they can be used to assemble a full double stranded DNA fragment encompassing the ecotropic envelope sequence between and including part of the ecoenv17 and ecoenv12 oligonucleotide sequences. This is done by first purifying the two fragments from the primary PCR using Qiaquick PCR purification columns to remove all remaining primers followed by doing a PCR using the two overlapping fragments, and primers ecoenv17 and ecoenv12, and all the components necessary for DNA amplification using Elongase. This step results in the assembly of a fragment harboring the 12 mer hCAT1 binding peptide insertions and results in the deletion of the LTSLTP (SEQ. ID. NO. 40) or PFSS (SEQ. ID. NO. 39) sequence. These fragments are purified and digested with NotI and PinA1, resulting in a DNA fragment of approximately 519 base pairs which was isolated from an agarose gel using Qiagen DNA isolation kit. The 519 base pair fragments were then ligated into a NotI and PinA1 digested gpIII/env2 Surfscript fragment of approximately 4000 base pairs using T4 ligase as described above in Example 3. E. coli bacteria are then transformed with the ligation mixture, ampicillin colonies picked, and plasmid DNA were isolated and analyzed for the presence of 519 base pair inserts using Not1 and PinA1 restriction enzymes and DNA agarose gel electrophoresis. Plasmids with appropriate inserts were then further verified by automated DNA sequencing of the inserts (Baseclear, Leiden, NL).

Phages displaying envelope with the various peptide inserts can then be produced and tested for their binding to and entry of hCAT1 expressing cells and compared to phages displaying the gpIII/env2 construct. The hCAT1 binding envelopes can then be used to develop retroviral vectors produced by mammalian cell lines.

Example 5

Soluble FAb Generation and Binding to Human Cells

To prepare soluble FAb fragments of the hCAT1 binding FAb phage clone, periplasmic fractions were made from HB2151 bacteria infected with clone # 25 phage. Infected bacteria were grown in LB medium with 2% glucose and 100 mg/ml ampicillin (LBGA) overnight while shaking at 30° C. The next day the infected cells were diluted 1:100 in 50 ml fresh LBGA and grown at 37° C. until the $OD_{600}$ was 0.8. Bacteria were then pelleted, followed by resuspension in 25 ml LB, 100 mg/ml ampicillin and 1 mM IPTG and incubation for 3 hours at 30° C. while shaking vigorously. Then the bacteria were pelleted and resuspended in 1 ml ice-cold PBS followed by a 14–16 hour incubation at 4° C. while rotating. The next day the periplasmic fraction was cleared from bacterial residues by centrifugation: once for 10 minutes at 8000 rpm C (Eppendorf centrifuge #5402) at 4° C. followed by a spin of 10 minutes at 14000 rpm, 4° C. Then the FAb periplasmic fractions were aliquoted and stored at −20° C. The presence and expression of FAb fragments was confirmed by doing a dot blot and probing for human kappa light chains with anti-human kappa polyclonal rabbit antibodies (Dako A0191, 1:1000 dilution, 60 minutes) and anti rabbit IgG (H+L) antibodies conjugated with horse radish peroxidase (Biorad, 170–6515, 1:20.000, 60 minutes). Each step was followed by washing 6 times with PBS, 0.05% Tween 20 (v/v). Final detection of human FAbs was done using ECL staining (Amersham). This revealed the presence of high concentrations of soluble FAb fragment of hCAT1 binding clone # 25. Dilutions of antibodies were made in PBS, 0.5% BSA (w/v), 0.05% Tween 20 (v/v).

The FAb fractions made as described above were then used to perform flow cytometric analyses in 911-hCAT1-k08 cells expressing hCAT1 and compared to phages displaying clone 25 (see, Example 3) (FIG. 17). For this purpose, cells were incubated with 100 ml periplasmic fraction of clone 25 or control clone for 1 hour at room temperature followed by washing twice with PBS, 0.1% BSA and incubation with 500 times diluted anti-human kappa light chain antibodies (see, above) for 30 minutes at room temperature. This was followed by washing twice with PBS/0.1% BSA and a 30 minute room temperature incubation with goat-anti-rabbit immunoglobulin antibodies conjugated with phycoerythrin (diluted in 1:20 in PBS/0.1% BSA, Sigma P9795) and measurement in a flow cytometer. Detection of phage binding was done as described under Example 2.

Clearly, FAb preparations of clone 25 bind to hCAT1 expressing cells, whereas FAb fragments of an irrelevant CHO cell binding clone did not. The results are very similar to the results observed with phages displaying FAb clone 25 (FIG. 17). Compared to phages displaying hCAT1 binding FAb 25, FAb fragments of clone 25 facilitate the measurement of hCAT1 in a multiparameter setting such as $CD34^+$ or $CD34^+lin^-$ cells.

Example 6
Generation of Adenoviral Vectors Displaying hCAT1 Binding Peptide Sequences in their Fiber Sequences Adenoviral vectors displaying hCAT1 binding sequences such as those described in Examples 2 and 3 are useful in stem cell gene therapy but also for other applications where a broad tropism is desired such as other gene therapy applications where local administration of the vector is used but where the primary tissue or cells are difficult to transduce with an adenoviral vector. Also these vectors can be used in functional genomics applications where gene or nucleic acid libraries are built in an adenoviral vector system and where transduction of as many cell types as possible is desired. For these purposes we included the peptide sequences describe in examples 2 and 3 in the H-I loop of adenovirus with serotype 5 (Xia et al., Structure, 1994 Dec 15; 2(12): 1259–70).

Figure 18:
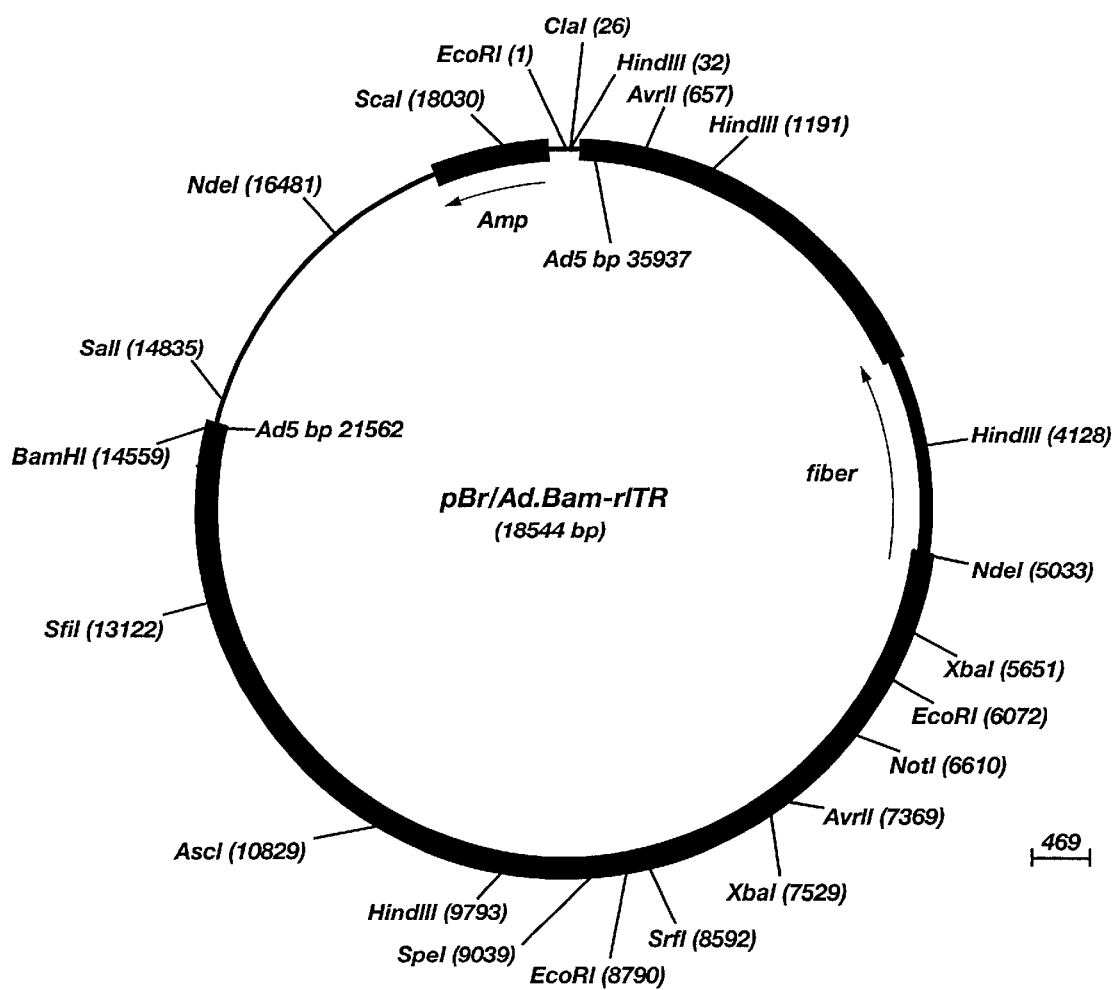
FIG. 18 depicts construct pBr/Ad.Bam-rITR as described herein.
Figure 19:
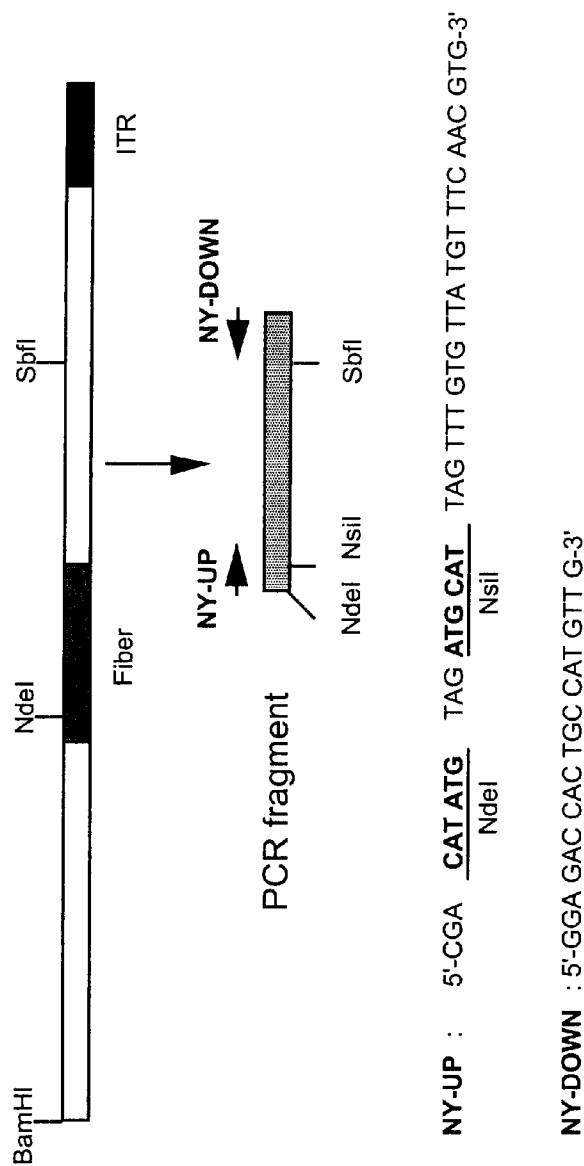
FIG. 19 graphically relates to the performance of a PCR with oligonucleotides "NY-up" (SEQ. ID. No. 71) and "NY-down" (SEQ. ID. No. 72) as described herein.
Figure 20:
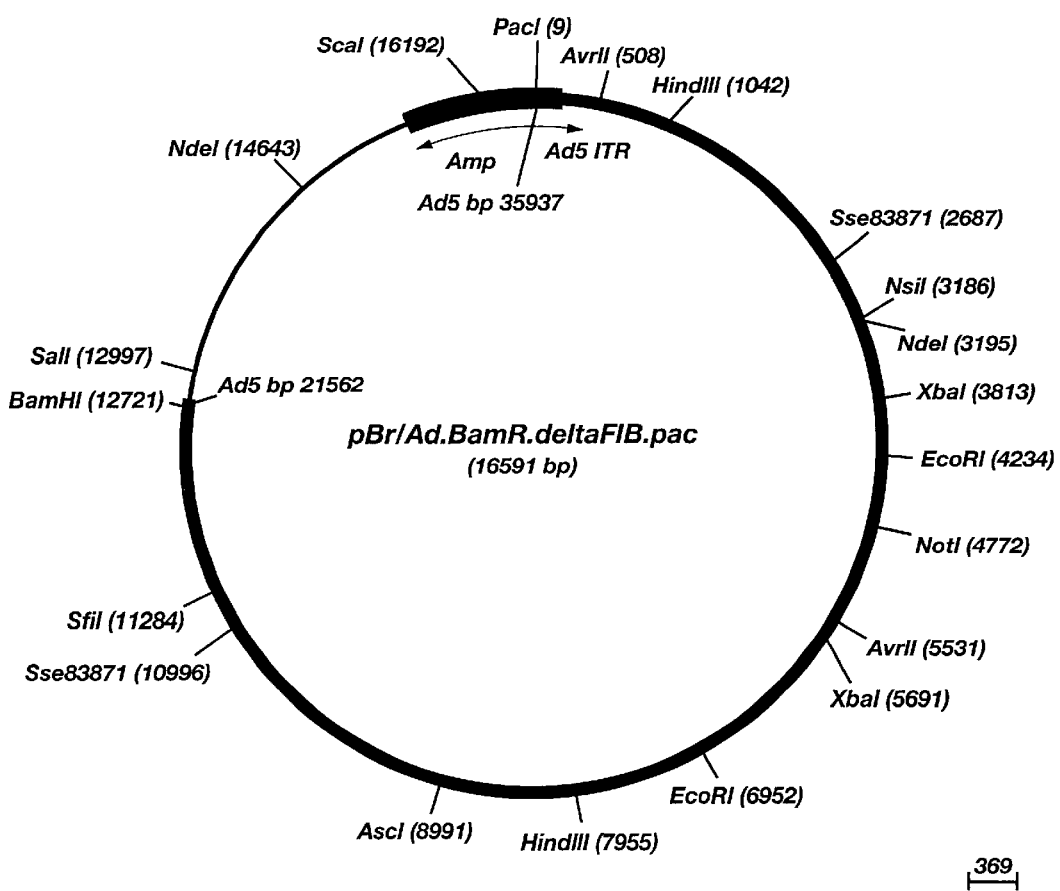
FIG. 20 depicts construct pBr/Ad.BamR.ΔFIB.pac.

Generation of Adenovirus Template Clones Lacking DNA Sequences Encoding for Adenoviral Fiber The fiber coding sequence of adenovirus serotype 5 ("Ad5") is located between nucleotides 31042 and 32787. To remove the Ad5 DNA encoding fiber, we started with construct pBr/Ad.Bam-rITR (FIG. 18; ECACC deposit P97082122). From this construct, the first step was the removal of an NdeI site. pBr322 plasmid DNA was digested with NdeI, after which protruding ends were filled using Klenow enzyme. This pBr322 plasmid was then religated, digested with NdeI and transformed into *E. coli* DH5α. The obtained pBr/ΔNdeI plasmid was digested with ScaI and SalI and the resulting 3198 bp vector fragment was ligated to the 15349 bp ScaI-SalI fragment derived from pBr/Ad.Bam-rITR, resulting in plasmid pBr/Ad.Bam-rITRΔNdeI which hence contained a unique NdeI site. Next a PCR was performed with oligonucleotides "NY-up" and "NY-down" (FIG. 19). During amplification, both an NdeI and an NsiI restriction site were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up and NY-down, 2 mM dNTP, PCR buffer with 1.5 mM $MgCl_2$, and 1 unit of Elongase heat stable polymerase (Life Technologies, Breda, NL). One-tenth of the PCR product was run on an agarose gel which demonstrated that the expected DNA fragment of about 2200 bp was amplified. This PCR fragment was subsequently purified using the Geneclean kit system for DNA purification (Bio101 Inc.) Then, both the construct pBr/Ad.Bam-rITRΔNdeI as well as the PCR product were digested with restriction enzymes NdeI and SbfI. The PCR fragment was subsequently cloned using T4 ligase enzyme into the NdeI and SbfI sites, thus generating pBr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pWe/Ad.AflII-EcoRI (described below) digested with PacI and EcoRI and a pBr/Ad.BamRΔFib construct in which heterologous fiber sequences have been inserted. To increase the efficiency of virus generation, the construct pBr/Ad.BamRAFib was modified to generate a PacI site flanking the right ITR. Hereto, pBr/Ad.BamRΔFib was digested with AvrII and the 5 kb adenoviral fragment was isolated and introduced into the vector pBr/Ad.Bam-rITR.pac#8 (ECACC deposit P97082121)_replacing the corresponding AvrII fragment. The resulting construct was named "pBr/Ad.BamR.ΔFIB.pac" (FIG. 20).

Once a heterologous fiber sequence is introduced in pBr/Ad.BamRΔFib.pac, the fiber modified right hand adenovirus clone may be introduced into a large cosmid clone. Such a large cosmid clone allows generation of adenovirus by only one homologous recombination, thus making the process extremely efficient.

Generation of Chimeric Adenoviral DNA Constructs

For the insertion of hCAT1 binding peptide sequences in the HI loop of Ad5 two fragments were amplified (primary PCR) using Elongase polymerase and the following two pairs of primers: Fragment 1: NdeIad5-1 (sense primer, Table 6 ) plus one of the AS (odd numbered) primers in Table 6. Fragment 2: NsiIAd5-1 (antisense primer, Table 6) plus one of the sense (even numbered) primers in Table 6.

Amplification for all PCRs consisted of a single hot start of 4 min at 94° C. followed by 30 cycles of each 30 sec. at 94° C., 30 sec. at 49° C., and 2 min. at 68° ending with a 7 minute period at 68°. The PCR reaction contained 25 pmol of oligonucleotides NY-up and NY-down, 2 mM dNTP, PCR buffer with 1.5 mM $MgCl_2$, and 1 unit of Elongase heat stable polymerase (Life Technologies, Breda, NL).

Figure 21:
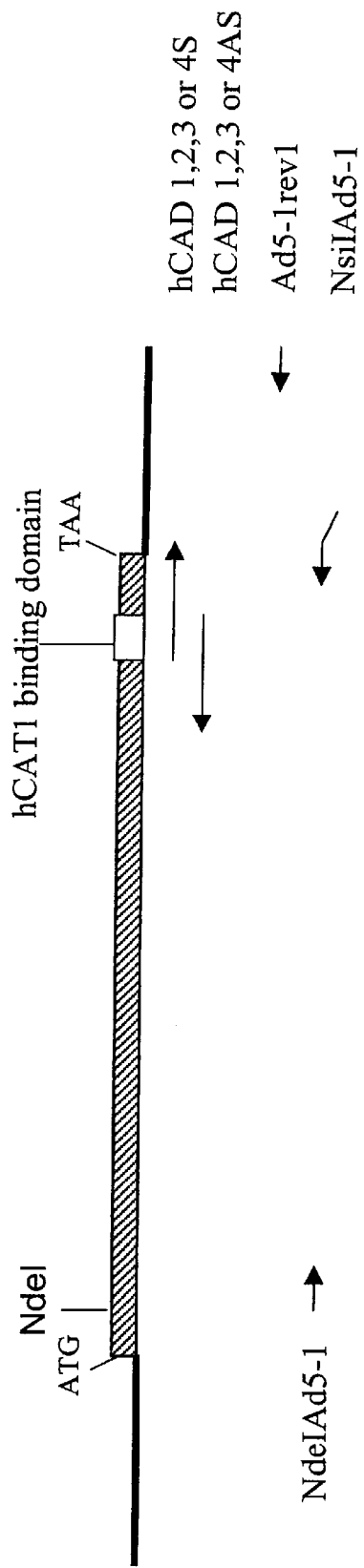
FIG. 21 graphically depicts FIBER Ad5 as described herein.

Fragment 1 harbors at the DNA level the 3' end the hCAT1 binding sequences, whereas fragment 2 harbors the peptide insertions at the 5' end. Since both fragments have now overlapping 3' (fragment 1) and 5' ends (fragment 2), they can be used to assemble a full double stranded DNA fragment encompassing one of the insertions (designated in hCAD1, hCAD2, hCAD3 or hCAD4 for h<u>CA</u>T1 binding and A<u>D</u>enovirus). FIG. 21 schematically depicts the method and primers used to generate the primary PCR products and assembly PCR. This is done by first running the crude PCR products on a 1% agarose gel (TAE) isolating the two fragments from the primary PCR out of a gel-slice using a Qiagen DNA isolation kit to remove all remaining primers and original template. This procedure was followed by a second "assembly" PCR using the two overlapping fragments, and two outer primers NdeIad5-1 (5') and NsiIAd5-1 (3'), and all the components necessary for DNA amplification using Elongase. This step results in the assembly of a fragment harboring the 12 mer hCAT1 binding peptide insertions and linker.

Oligonucleotide Ad5-1rev1 was designed for an alternative assembly PCR strategy. The primary PCR of fragment 2 results in a PCR product of 633 bp harboring the 12 mer hCAT1 binding peptide insertions. Assembly PCR using this fragment and the 5' fragments generated as described above ("fragment 1") results in an assembled fragment of 2271 bp which is easier to distinguish from the 5' primary fragment 1. The secondary assembly fragments were purified and digested with NdeI and NsiI resulting in a DNA fragment of 1736 base pairs. This fragment was isolated from a 1% agarose gel (TAE) using a Qiagen DNA isolation kit. The 1736 base pair fragments were then ligated into an NdeI and NsiI digested fragment of approximately 16853 base pairs derived from pBr/Ad.BamRΔFib.pac using T4 ligase. Electrocompetent *E. coli* bacteria (XL1 blue, Stratagene, >$10^{10}$/microgram plasmid DNA) were then electroporated with the ligation mixture, ampicillin resistant colonies picked, and plasmid DNA were isolated and analyzed for the presence of 1736 base pair inserts using NdeI and NsiI restriction enzymes and DNA agarose gel electrophoresis. Plasmids with appropriate inserts were then further verified by automated DNA sequencing of the inserts.

Generation of Recombinant Adenovirus Chimeric for Fiber Protein

To enable efficient generation of chimeric viruses, transfection using pClipsal/lacZ, pWE/Ad.AflII-Eco and pBr/Ad.Bam-rITR.PacI-hCAD1,2,3 or 4 fib5 was performed. pBr/Ad.Bam-rITR.PacI-hCAD1,2,3 or 4 fib5 all have a PacI site near the right ITR that enables the ITR to be separated from the vector sequences and allows efficient initiation of adenoviral replication after the complete vector molecule has been generated after double homologous recombination. The plasmid pClipsal/lacZ was generated as follows.

Generation of pAd5/ClipsalLacZ

First, a PCR fragment was generated from pZipADMo+ PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ. ID. NO. 4) and LTR-2: 5'-GCG GAT CCT TCG AAC CAT GGT AAG CTT GGT ACC GCT AGC GTT AAC CGG GCG ACT CAG TCA ATC G-3' (SEQ. ID. NO. 5). Pwo DNA polymerase (Boehringer Mannheim) was used according to manufacturer's protocol with the following temperature cycles: once 5'at 95° C.; 3' at 55° C.; and 1' at 72° C., and 30 cycles of 1' at 95° C., 1' at 60° C., 1' at 72° C., followed by once 10' at 72° C. The PCR product was then digested with BamHI and ligated into pMLP10 (Levrero et al., 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990) using the following primers: HSA1, 5'-GCG CCA CCA TGG GCA GAG CGA TGG TGG C-3' (SEQ. ID. NO. 6) and HSA2, 5'-GTT AGA TCT AAG CTT GTC GAC ATC GAT CTA CTA ACA GTA GAG ATG TAG AA-3' (SEQ. ID. NO. 7). The 269 bp amplified fragment was sub-cloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as an NcoI(sticky)-SalI (blunt) fragment and cloned into the 3.5 kb NcoI(sticky)/BstBI(blunt) fragment from pLTR10, resulting in pLTR-HSA10.

Finally, pLTR-HSA10 was digested with EcoRI and BamHI, after which the fragment containing the left ITR, packaging signal, L420 promoter and HSA gene was inserted into vector pMLPI.TK (described in PCT Internet'l Patent Appl'n WO 97/00326) digested with the same enzymes and thereby replacing the promoter and gene sequences. This resulted in the new adapter plasmid pAd/LA420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII, followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII and followed by treatment with T4 DNA polymerase. This adapter plasmid was named pCLIP.

To enable removal of vector sequences from the left ITR in pAdS/Clip (described in Example 2B), this plasmid was partially digested with EcoRI and the linear fragment was isolated. An oligo of the sequence 5' TTAAGTCGAC-3' (SEQ. ID. NO. 10) was annealed to itself, resulting in a linker with an SalI site and EcoRI overhang. The linker was ligated to the partially digested pAd5/Clip vector and clones were selected that had the linker inserted in the EcoRI site, 23 bp upstream of the left adenovirus ITR in pAdS/Clip, resulting in pAdS/Clipsal.

The adapter plasmid pAdS/Clipsal.LacZ was generated as follows: The *E. coli* LacZ gene was amplified from the plasmid pMLP.nlsLacZ (EP 95–202 213) by PCR with the primers: 5' GGGGTGGCCAGGGTACCTCTAG-GCTTTTGCAA (SEQ. ID. NO. 9) and 5' GGGGGGATC-CATAAACAAGTTCAGAATCC (SEQ. ID. NO. 10). The PCR reaction was performed Ex Taq (Takara) according to the supplier's protocol at the following amplification program: 5 minutes 94° C., 1 cycle; 45 seconds 94° C. and 30 seconds 60° C. and 2 minutes 72° C., 5 cycles; 45 seconds 94° C. and 30 seconds 65° C. and 2 minutes 72° C., 25 cycles; 10 minutes 72; 45 seconds 94° C. and 30 seconds 60° C. and 2 minutes 72° C., 5 cycles, I cycle. The PCR product was subsequently digested with KpnI and BamHI and the digested DNA fragment was ligated into KpnI/BamHI digested pcDNA3 (Invitrogen), giving rise to pcDNA3.nlsLacZ. Next, the plasmid pAd5/Clipsal was digested with SpeI. The large fragment containing part of the 5' part CMV promoter and the adenoviral sequences was isolated. The plasmid pcDNA3.nlsLacZ was digested with SpeI and the fragment containing the 3' part of the CMV promoter and the lacZ gene was isolated. Subsequently, the fragments were ligated, giving rise to pAd/Clipsal.LacZ.

pWE/Ad.AflII-EcoRI was generated as follows. Cosmid vector pWE15 (Clontech) was used to clone larger Ad5 inserts. First, a linker containing a unique PacI site was inserted in the EcoRI sites of pWE15 creating pWE.pac. pWE.pac was digested with ClaI and 5' protruding ends were filled using Klenow enzyme. The DNA was then digested with PacI and isolated from agarose gel. pWE/Ad.AflII-rITR (ECACC deposit P97082116) was digested with EcoRI after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultra-competent XL10-Gold cells from Stratagene, clones were identified that contained the expected insert. pWE/AflII-EcoRI contains Ad5 sequences from bp 3534–27336.

Figure 22:
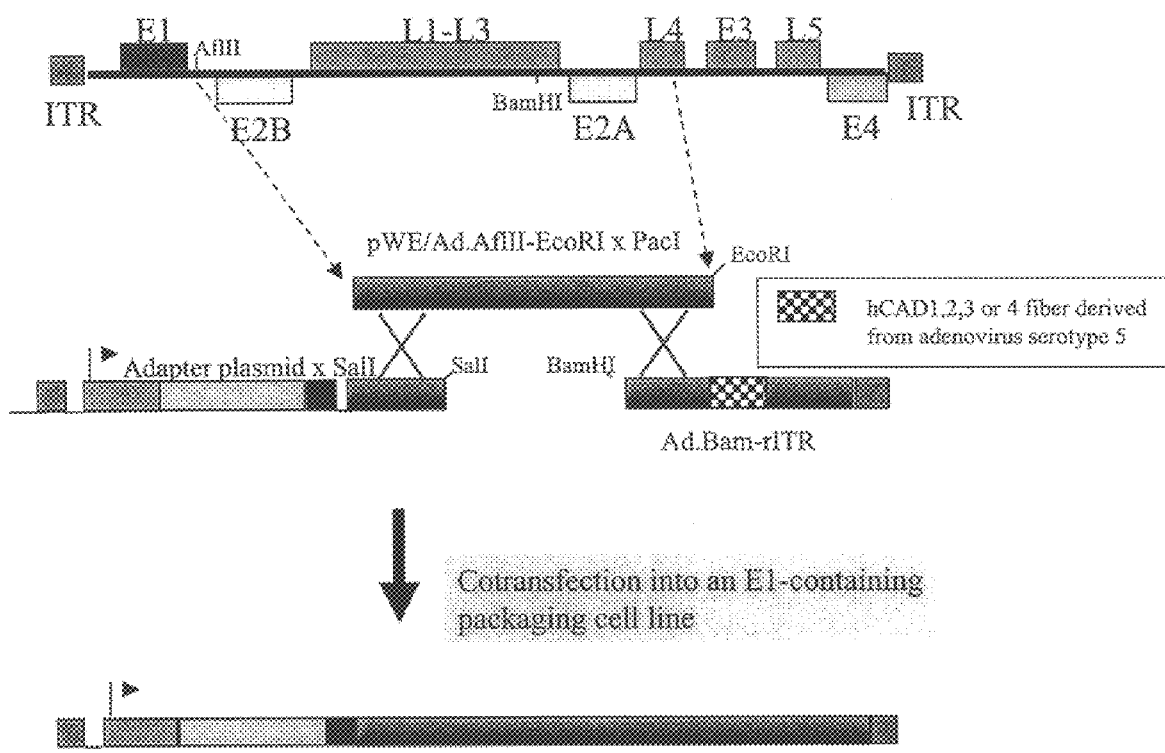
FIG. 22 schematically depicts the method and fragments used to generate the chimeric viruses.

Before transfection, the three necessary DNA constructs were treated as follows: pClipsal/lacZ was linearized by digestion with SalI; pWE/Ad.AflII-Eco was digested with PacI and EcoRI; and the four different pBr/Ad.Bam-rITR.PacI-hCAD1,2,3 or 4 fib5 constructs were digested with BamHI and PacI. These three digested DNA preparations were transfected into PER.C6 to generate recombinant adenovirus. FIG. 22 schematically depicts the method and fragments used to generate the chimeric viruses. Alternatively, other adapter fragments containing a different marker gene or stronger promoter could be used.

For transfection, 2 μg of pCLIPsal/lacZ and 4 μg total of pWE/Ad.AflII-Eco and 2 μg of one of the four different pBr/Ad.Bam-rITR.PacI-hCAD1, 2, 3 or 4 fib5 constructs were diluted in serum free DMEM to 100 μl total volume. To this DNA suspension 100 μl 2.5 times diluted lipo-fectamine (Life Technologies) in serum-free DMEM medium was added. After 30 minutes at room temperature, the DNA-lipofectamine complex solution was added to 2.3 ml of serum-free DMEM. This mixture was then added to a culture flask with a surface area of 25 cm² (T25). This T25 flask was seeded with PER.C6 cells 24-hours prior to transfection at a density of 3.5×10⁶ cells/flask. Two hours later, the DNA-lipofectamine complex containing medium was diluted by the addition of 2.5 ml DMEM supplemented with 10% foetal bovine serum. Again, 24 hours later, the medium was replaced by fresh DMEM supplemented with 10% foetal bovine serum. On day 2 after transfection, the cells were passed to a tissue culture flask (T80) with a surface area of 80 cm². Cells were subsequently cultured for 4–14 days. During this period the medium was replaced with fresh medium upon medium depletion and/or reaching confluency. At full CPE the virus was harvested by one freeze/thaw cycle. Part of the supernatant was used to reinfect a T80 flask with PER.C6 cells. This propagation resulted in viruses displaying hCAT1 binding sequences carrying a lacZ as a marker gene. These virus-preparations were then used to transduce hCAT1 expressing cells including human and non-human primate hemopoietic stem cells, such as human smooth muscle cells, human chorion villi cells, human primary tumor cells, human and mouse fibroblasts, human synoviocytes and compared to the transduction efficiency of adenovirus 5 vector without the hCAT1 binding peptide insertions but with the introduced NdeI and NsiI sites.

For those skilled in the art, modifications and variations of the methods and materials described herein will be obvious. As an example, but by no means intended as a limitation, other desired therapeutic transgenes can be incorporated in adenoviral vectors displaying the hCAT1 binding peptide sequences described herein such as the cDNA for endothelial nitric oxide synthase or libraries of nucleic sequences either as pools or as collections of individual clones made either manually or using automated procedures.

REFERENCES

Albritton, L. M., Kim, J. W., Tseng, L. and Cunningham, J. M. (1993) Envelope-binding domain in the cationic amino acid transporter determines the host range of ecotropic murine retroviruses. *J. Virol.* 67(4):2091–2096.

Albritton, L. M., Tseng, L., Scadden, D. and Cunningham, J. M. (1989) A putative murine ecotropic retrovirus receptor gene encodes a multiple membrane-spanning protein and confers susceptibility to virus infection. *Cell* 57(4):659–666.

Battini, J. L., Heard, J. M. and Danos, O. (1992) Receptor choice determinants in the envelope glycoproteins of amphotropic, xenotropic, and polytropic murine leukemia viruses. *J. Virol.* 66(3): 1468–75.

Chomczynski, P. and Sacchi, N. (1987) Single-step method of RNA isolation by acid guanidinium thiocyanate-phenol-chloroform extraction. *Anal Biochem* 162(1):156–9.

Closs, E. I., Rinkes, I. H., Bader, A., Yarmush, M. L. and Cunningham, J. M. (1993) Retroviral infection and expression of cationic amino acid transporters in rodent hepatocytes. *J. Virol.* 67(4):2097–102.

Demarquoy, J. (1993) Retroviral-mediated gene therapy for the treatment of citrullinemia. Transfer and expression of argininosuccinate synthetase in human hematopoietic cells. *Experientia* 49(4):345–8.

Fass, D., Davey, R. A., Hamson, C. A., Kim, P. S., Cunningham, J. M. and Berger, J. M. (1997) Structure of a murine leukemia virus receptor-binding glycoprotein at 2.0 angstrom resolution. *Science* 277(5332):1662–6.

Gordon, E. M. and Anderson, W. F. (1994) Gene therapy using retroviral vectors. *Curr Opin Biotechnol* 5(6):611–6.

Gunzburg, W. H. and Salmons, B. (1996) Development of retroviral vectors as safe, targeted gene delivery systems. *J Mol Med* 74(4):171–82.

Havenga, M., Hoogerbrugge, P., Valerio, D. and van Es, H. H. G. (1997) Retroviral stem cell gene therapy. *Stem cells* 15(3):162–179.

Hoogerbiugge, P. M., van Beusechem, V. W., Fischer, A., Debree, M., Le Deist, F., Perignon, J. L., Morgan, G., Gaspar, B., Fairbanks, L. D., Skeoch, C. H., Mosely, A., Harvey, M., Levinskey, R. J. and Valerio, D. (1996) Bone marrow gene transfer in three patients with adenosine deaminase deficiency. *Gene Therapy* 3, 179–183.

Januszeski, M. M., Cannon, P. M., Chen, D., Rozenberg, Y. and Anderson, W. F. (1997) Functional analysis of the cytoplasmic tail of Moloney murine leukemia virus envelope protein. *J. Virol.* 71(5):3613–9.

Kafri, T., Blomer, U., Peterson, D. A., Gage, F. H. and Verma, I. M. (1997) Sustained expression of genes delivered directly into liver and muscle by lentiviral vectors. *Nat Genet* 17(3):314–7.

Kavanaugh, M. P., Miller, D. G., Zhang, W., Law, W., Kozak, S. L., Kabat, D. and Miller, A. D. (1994) Cell-surface receptors for gibbon ape leukemia virus and amphotropic murine retrovirus are inducible sodium-dependent phosphate symporters. *Proc Natl Acad Sci U S A* 91(15):7071–5 issn: 0027–8424.

Kim, J. W., Closs, E. I., Albritton, L. M. and Cunningham, J. M. (1991) Transport of cationic amino acids by the mouse ecotropic retrovirus receptor. *Nature* 352(6337):725–728.

Kim, V. N., Mitrophanous, K., Kingsman, S. M. and Kingsman, A. J. (1998) Minimal requirement for a lentivirus vector based on human immunodeficiency virus type 1. *J. Virol.* 72(1):811–6.

Knaan-Shanzer, S., Valerio, D. and van Beusechem, V. W. (1996) Cell cycle state, response to hemopoietic growth factors and retroviral vector-mediated transduction of human hemopoietic stem cells. *Gene Ther* 3(4):323–333.

Krasnykh, V., Dmitriev, I., Mikheeva, G., Miller, C. R., Belousova, N. and Curiel, D. T. (1998) Characterization of an adenovirus vector containing a heterologous peptide epitope in the HI loop of the fiber knob. *J. Virol.* 72(3): 1844–52.

MacKrell, A. J., Soong, N. W., Curtis, C. M. and Anderson, W. F. (1996) Identification of a subdomain in the Moloney murine leukemia virus envelope protein involved in receptor binding. *J. Virol.* 70(3):1768–74.

Malhotra, S., Scott, A. G., Zavorotinskaya, T. and Albritton, L. M. (1996) Analysis of the murine ecotropic leukemia virus receptor reveals a common biochemical determinant on diverse cell surface receptors that is essential to retrovirus entry. *J. Virol.* 70(1):321–326.

Masuda, M., Hanson, C. A., Alvord, W. G., Hoffman, P. M., Ruscetti, S. K. and Masuda, M. (1996a) Effects of subtle changes in the SU protein of ecotropic murine leukemia virus on its brain capillary endothelial cell tropism and interference properties. *Virology* 215(2):142–51 Issn: 0042–6822.

Masuda, M., Masuda, M., Hanson, C. A., Hoffman, P. M. and Ruscetti, S. K. (1996b) Analysis of the unique hamster cell tropism of ecotropic murine leukemia virus PVC-21 1. *J. Virol.* 70(12):8534–8539.

McClure, M. O., Sommerfelt, M. A., Marsh, M. and Weiss, R. A. (1990) The pH independence of mammalian retrovirus infection. *J Gen Virol* 71(Pt 4):767–773.

McGuiness, B. T., Walter, G., FitzGerald, K., Schuler, P., Mahoney, W., Duncan, A. R. and Hoogenboom, H. R.

(1996) Phage diabody repertoires for selection of large numbers of bispecific antibody fragments. *Nat Biotechnol* 14, 1149–1154.

Miller, D. G. and Miller, A. D. (1994) A family of retroviruses that utilize related phosphate transporters for cell entry. *J. Virol.* 68(12):8270–6 issn: 0022-538x.

Miyoshi, H., Takahashi, M., Gage, F. H. and Verma, I. M. (1997) Stable and efficient gene transfer into the retina using an HIV-based lentiviral vector. *Proc Natl Acad Sci U S A* 94(19):10319–23.

Naldini, L., Blomer, U., Gage, F. H., Trono, D. and Verma, I. M. (1996a) Efficient transfer, integration, and sustained long-term expression of the transgene in adult rat brains injected with a lentiviral vector. *Proc Natl Acad Sci U S A* 93(21): 11382–8.

Naldini, L., Blomer, U., Gallay, P., Ory, D., Mulligan, R., Gage, F. H., Verma, I. M. and Trono, D. (1996b) In vivo gene delivery and stable transduction of nondividing cells by a lentiviral vector [see comments]. *Science* 272(5259):263–7.

Orlic, D., Girard, L. J., Jordan, C. T., Anderson, S. M., Cline, A. P. and Bodine, D. M. (1996) The level of mRNA encoding the amphotropic retrovirus receptor in mouse and human hematopoietic stem cells is low and correlates with the efficiency of retrovirus transduction. *Proc Natl Acad Sci U S A* 93(20):11097–11102.

Poeschla, E., Corbeau, P. and Wong-Staal, F. (1996) Development of HIV vectors for anti-HIV gene therapy. *Proc Natl Acad Sci U S A* 93(21): 11395–9.

Rizvi, T. A. and Panganiban, A. T. (1992) Simian immunodeficiency virus vectors: replication and pseudotyping. *J Med Primatol* 21(2–3):69–73.

Skov, H. and Andersen, K. B. (1993) Mutational analysis of Moloney murine leukemia virus surface protein gp70. J-Gen-Virol 74(Pt 4):707–14.

Sullivan, D. E., Dash, S., Du, H., Hiramatsu, N., Aydin, F., Kolls, J., Blanchard, J., Baskin, G. and Gerber, M. A. (1997) Liver-directed gene transfer in non-human primates. *Hum Gene Ther* 8(10): 1195–206.

Thomas,. A, Gray, K. D. and Roth, M. J. (1997) Analysis of mutations within the cytoplasmic domain of the Moloney murine leukemia virus transmembrane protein. *Virology* 227(2):305–13.

Van Beusechem, V. W., Bakx, T. A., Kaptein, L. C., Bart-Baumeister, J. A., Kukler, A., Braakman, E. and Valerio, D. (1993) Retrovirus-mediated gene transfer into rhesus monkey hematopoietic stem cells: the effect of viral titers on transduction efficiency. *Hum Gene Ther* 4(3):239–47.

van Beusechem, V. W., Kukler, A., Heidt, P. J. and Valerio, D. (1992) Long-term expression of human adenosine deaminase in rhesus monkeys transplanted with retrovirus-infected bone-marrow cells. *Proc Natl Acad Sci U S A* 89(16):7640–4.

van Es, H. H. G., Knaan, S., Camphorst, S., Verlinden, S. and Valerio, D. (1996) Expression studies of the amphotropic receptor GLVR2 in mammalian cells and tissues including human CD34+cells. Cold Spring Harbor Gene therapy meeting, Abstract 309.

van Zeiji, M., Johann, S. V., Closs, E., Cunningham, J., Eddy, R., Shows, T.B. and O'Hara, B. (1994) A human amphotropic retrovirus receptor is a second member of the gibbon ape leukemia virus receptor family. *Proc Natl Acad Sci U S A* 91(3):1168–72 issn: 0027–8424.

Vile, R. G., Tuszynski, A. and Castleden, S. (1996) Retroviral vectors. From laboratory tools to molecular medicine. *Mol Biotechnol* 5(2): 139–58.

von Kalle, C., Kiem, H. P., Goehle, S., Darovsky, B., Heimfeld, S., Torok Storb, B., Storb, R. and Schuening, F. G. (1994) Increased gene transfer into human hematopoietic progenitor cells by extended in vitro exposure to a pseudotyped retroviral vector. *Blood* 84(9):2890–7 issn: 0006–4971.

Weiss, R. A. (1996) Retrovirus classification and cell interactions. *J Antimicrob Chemother* 37 Suppl B, 1–11.

Wilson, C. A., Farrell, K. B. and Eiden, M. V. (1994) Properties of a unique form of the murine amphotropic leukemia virus receptor expressed on hamster cells. *J. Virol.* 68(12):7697–703 issn: 0022-538x.

Yoshimoto, T., Yoshimoto, E. and Meruelo, D. (1991) Molecular cloning and characterization of a novel human gene homologous to the murine ecotropic retroviral receptor. *Virology* 185(1): 10–17.

Yoshimoto, T., Yoshimoto, E. and Meruelo, D. (1993) Identification of amino acid residues critical for infection with ecotropic murine leukemia retrovirus. *J. Virol.* 67(3):1310–4 Issn: 0022-538x.

TABLE 1

| Selection | Stringent selection | | | Non-stringent selection | | |
| --- | --- | --- | --- | --- | --- | --- |
| | Input phages | Output phages | Output input | Input phages | Output phages | Output input |
| 500 nanoM peptide | $1.4 \times 10^{10}$ | $0.6 \times 10^5$ | $4.3 \times 10^{-6}$ | $1.4 \times 10^{10}$ | $1.5 \times 10^5$ | $1.1 \times 10^{-5}$ |
| 500 nanoM peptide | $3.8 \times 10^9$ | $1.1 \times 10^5$ | $2.9 \times 10^{-4}$ | $3.8 \times 10^8$ | $9.8 \times 10^5$ | $2.6 \times 10^{-3}$ |
| 500 nanoM peptide | $7.6 \times 10^7$ | $3 \times 10^4$ | $3.9 \times 10^{-4}$ | $3.8 \times 10^7$ | $9.0 \times 10^3$ | $2.4 \times 10^{-1}$ |
| 500 nanoM peptide | $2.1 \times 10^8$ | $6 \times 10^5$ | $2.9 \times 10^{-3}$ | $1.1 \times 10^8$ | $6.8 \times 10^5$ | $6.2 \times 10^{-3}$ |
| 100 nanoM peptide | $5.3 \times 10^{10}$ | $2.4 \times 10^9$ | $4.5 \times 10^{-2}$ | $6.7 \times 10^{10}$ | $1.5 \times 10^9$ | $2.2 \times 10^{-2}$ |
| 100 nanoM peptide | $1.2 \times 10^{11}$ | $1.8 \times 10^{10}$ | $1.5 \times 10^{-1}$ | $1.0 \times 10^{11}$ | $5.0 \times 10^{10}$ | $5.0 \times 10^{-1}$ |
| HCAT1 cells (k08) | $9.8 \times 10^{11}$ | $1.1 \times 10^6$ | $1.1 \times 10^{-6}$ | $1.1 \times 10^{12}$ | $7.2 \times 10^6$ | $6.5 \times 10^{-1}$ |
| HCAT1 cells (k08) | ND | $2 \times 10^4$ | | | | |
| HCAT1 cells (k08) | $2.6 \times 10^{10}$ | $2.1 \times 10^5$ | $8.1 \times 10^{-6}$ | | | |

TABLE 2

| Round | Target | Insert Sequence | No. of identical clones |
| --- | --- | --- | --- |
| Amplified library | None | EQSRPSWQLTPT (SEQ ID NO: 11) | 1 |
| | | QTHQLLRKPPSF (SEQ ID NO: 12) | 1 |
| | | YMHEPITPNPVT (SEQ ID NO: 13) | 1 |
| | | WHHIPNSAKISL (SEQ ID NO: 14) | 1 |

TABLE 2-continued

| Round | Target | Insert Sequence | No. of identical clones |
|---|---|---|---|
| | | SENLTLMTVLQM (SEQ ID NO: 15) | 1 |
| | | NLMPPPVPRLPL (SEQ ID NO: 16) | 1 |
| | | TPQGVHYHPNMR (SEQ ID NO: 17) | 1 |
| 1 | hCAT1 peptide | ND | |
| 2 | hCAT1 peptide | ND | |
| 3 | hCAT1 peptide | TLNNHTTPPAWN (SEQ ID NO: 18) | 1 |
| | | QVVHSPFPTSRP (SEQ ID NO: 19) | 1 |
| 4 | hCAT1 peptide | ND | |
| 5 | hCAT1 peptide | FEQHNWWDSHPQ (SEQ ID NO: 20) | 1 |
| | | NTFDLWLQSVPQ (SEQ ID NO: 21) | 7 |
| 6 | hCAT1 peptide | FEGCHPQSGLSC (SEQ ID NO: 22) | 1 |
| | | FEQHNWWDSHPQ (SEQ ID NO: 20) | 1 |
| | | NTFDLWLQSVPQ (SEQ ID NO: 21) | 5 |
| | | SVSVGMKPSPRP (SEQ ID NO: 1) | 4 |
| 1 | hCAT1 cells | SVSVGMKPSPRP (SEQ ID NO: 1) | 4 |
| 2 | hCAT1 cells | SVSVGMKPSPRP (SEQ ID NO: 1) | 4 |
| 3 | hCAT1 cells | SVSVGMKPSPRP (SEQ ID NO: 1) | 23 |

TABLE 3

Binding and internalization of phages displaying peptide SVSVGMKPSPRP (SEQ ID NO: 1)

| | | | #pfu × 1000: | |
|---|---|---|---|---|
| Cell-line: | Temp: | Phage rescue: | clone #26 | 12-mer library |
| 911-hCAT1 | 37 C. | Elution | 120 | 4.32 |
| | | Lysis | 72 | 18.72 |
| 911-hCAT1 | 37 C. | Whole sample lysis | 205.2 | 88.2 |
| 911-pcDNA3 | 37 C. | Elution | 55.68 | 3.84 |
| | | Lysis | 47.52 | 8.64 |
| 911-pcDNA3 | 37 C. | Whole sample lysis | 216 | 0 |

TABLE 4

| Selection | Input phages | Output phages | Output/input ratio |
|---|---|---|---|
| 500 nanoM peptide | $2.7 \times 10^{12}$ | $9.0 \times 10^{5}$ | $3.6 \times 10^{-7}$ |
| 500 nanoM peptide | $5.7 \times 10^{12}$ | $2.0 \times 10^{6}$ | $3.3 \times 10^{-7}$ |
| 100 nanoM peptide | $9.5 \times 10^{12}$ | $1.5 \times 10^{10}$ | $1.6 \times 10^{-3}$ |
| 20 nanoM peptide | $7.0 \times 10^{12}$ | $3.7 \times 10^{10}$ | $5.2 \times 10^{-3}$ |
| hCAT1 cells (k08) | $7.0 \times 10^{12}$ | $3.0 \times 10^{5}$ | $4.4 \times 10^{-7}$ |

TABLE 4-continued

| Selection | Input phages | Output phages | Output/input ratio |
|---|---|---|---|
| hCAT1 cells (k08) | $5.4 \times 10^{12}$ | $1.7 \times 10^{7}$ | $3.1 \times 10^{-6}$ |
| hCAT1 cells (k08) | $5.4 \times 10^{12}$ | $1.5 \times 10^{7}$ | $2.8 \times 10^{-6}$ |

TABLE 5A

Insertion of hCAT1 binding peptides in LTSLTP or PFSS site of ecotropic murine leukemia envelope.

| Sequence (5'- . . . -3') | Description | Name 2 |
|---|---|---|
| tttgagcagcataattggtgggattcgcatcctcagcccccggggccccccttgt (SEQ ID NO: 23) | FEQHNWWDSHPO at PFSS (SEQ ID NO: 20) | Pepenv01 Sense |
| ctgaggatgcgaatcccaccaattatgctgctcaaaggattgatattctagccc (SEQ ID NO: 24) | FEQHNWWDSHPQ at PFSS (SEQ ID NO: 20) | Pepenv02 Anti |
| tttgagcagcataattggtgggattcgcatcctcagcggtgcaacactgcctgg (SEQ ID NO: 25) | FEQHNWWDSHPQ at LTSLTP (SEQ ID NO: 20) | Pepenv03 Sense |
| ctgaggatgcgaatcccaccaattatgctgctcaaaaggttcttcgcagtctct (SEQ ID NO: 26) | FEQHNWWDSHPQ at LTSLTP (SEQ ID NO: 20) | Pepenv04 Anti |
| aatacttttgatctttggctgcagtctgttcctcagcccccggggccccccttgt (SEQ ID NO: 27) | NTFDLWLQSVPQ at PFSS (SEQ ID NO: 21) | Pepenv05 Sense |
| ctgaggaacagactgcagccaaagatcaaaagtattggattgatattctagccc (SEQ ID NO: 28) | NTFDLWLQSVPQ at PFSS (SEQ ID NO: 21) | Pepenv06 Anti |
| aatacttttgatctttggctgcagtctgttcctcagcggtgcaacactgcctgg (SEQ ID NO: 29) | NTFDLWLQSVPQ at LTSLTP (SEQ ID NO: 21) | Pepenv07 Sense |
| ctgaggaacagactgcagccaaagatcaaaagtattaggttcttcgcagtctct (SEQ ID NO: 30) | NTFDLWLQSVPQ at LTSLTP (SEQ ID NO: 21) | Pepenv08 Anti |
| tctgtttctgtgggtatgaagccgagtcctaggcctcccccggggccccccttgt (SEQ ID NO: 31) | SVSVGMKPSPRP at PFSS (SEQ ID NO: 1) | Pepenv09 Sense |
| aggcctaggactcggcttcatacccacagaaacagaggattgatattctagccc (SEQ ID NO: 32) | SVSVGMKPSPRP at PFSS (SEQ ID NO: 1) | Pepenv10 Anti |
| tctgtttctgtgggtatgaagccgagtcctaggcctcggtgcaacactgcctgg (SEQ ID NO: 33) | SVSVGMKPSPRP at LTSLTP (SEQ ID NO: 1) | Pepenv11 Sense |
| aggcctaggactcggcttcatacccacagaaacagaaggttcttcgcagtctct (SEQ ID NO: 34) | SVSVGMKPSPRP at LTSLTP (SEQ ID NO: 1) | Pepenv12 Anti |
| tttgaggggtgtcatcctcagtcggggctgtcttgtcccccggggccccccttgt (SEQ ID NO: 35) | FEGCHPQSGLSC at PFSS (SEQ ID NO: 22) | Pepenv13 Sense |
| acaagacagccccgactgaggatgacacccctcaaaggattgatattctagccc (SEQ ID NO: 36) | FEGCHPQSGLSC at PFSS (SEQ ID NO: 22) | Pepenv14 Anti |
| tttgaggggtgtcatcctcagtcggggctgtcttgtcggtgcaacactgcctgg (SEQ ID NO: 37) | FEGCHPQSGLSC at LTSLTP(SEQ ID NO: 22) | Pepenv15 Sense |
| acaagacagccccgactgaggatgacacccctcaaaaggttcttcgcagtctct (SEQ ID NO: 38) | FEGCHPQSGLSC at LTSLTP (SEQ ID NO: 22) | Pepenv16 Anti |

TABLE 5B

Insertion of hCAT1 binding peptides in BstEII site of ecotropic murine leukemia envelope. Underlined sequences of peptide inserts indicate linker amino residues.

| Sequence (5'- . . . -3') | Peptide insert | Name 2 |
|---|---|---|
| atcacctgggaggtaaccggccatatgtttgagcagcataattggtgggattcg catcctcagggtgctagcttggtaaccaatggagatcg (SEQ ID NO: 41) | <u>GHM</u>FEQHNWWDSHPQ<u>GASLVT</u> (SEQ ID NO: 49) | Pepenv17 Sense |
| cgatctccattggttaccaagctagcaccctgaggatgcgaatcccaccaatta tgctgctcaaacatatggccggttacctcccaggtgat (SEQ ID NO: 42) | <u>GHM</u>FEQHNWWDSHPQ<u>GASLVT</u> (SEQ ID NO: 49) | Pepenv18 Anti |
| atcacctgggaggtaaccggccatatgaatactttgatctttggctgcagtct gttcctcagggtgctagcttggtaaccaatggagatcg (SEQ ID NO: 43) | <u>GHM</u>NTFDLWLQSVPQ<u>GASLVT</u> (SEQ ID NO: 50) | Pepenv19 Sense |
| cgatctccattggttaccaagctagcaccctgaggaacagactgcagccaaga tcaaagtattcatatggccggttacctcccaggtgat (SEQ ID NO: 44) | <u>GHM</u>NTFDLWLQSVPQ<u>GASLVT</u> (SEQ ID NO: 50) | Pepenv20 Anti |
| atcacctgggaggtaaccggccatatgtctgtttctgtgggtatgaagccgagt cctaggcctggtgctagcttggtaaccaatggagatcg (SEQ ID NO: 45) | <u>GHM</u>SVSVGMKPSPRP<u>GASLVT</u> (SEQ ID NO: 51) | Pepenv21 Sense |
| cgatctccattggttaccaagctagcaccaggcctaggactcggcttcataccc acagaaacagacatatggccggttacctcccaggtgat (SEQ ID NO: 46) | <u>GHM</u>SVSVGMKPSPRP<u>GASLVT</u> (SEQ ID NO: 51) | Pepenv22 Anti |
| atcacctgggaggtaaccggccatatgtttgaggggtgtcatcctcagtcgggg ctgtcttggtgctagcttggtaaccaatggagatcg (SEQ ID NO: 47) | <u>GHM</u>FEGCHPQSGLSC<u>GASLVT</u> (SEQ ID NO: 52) | Pepenv23 Sense |
| cgatctccattggttaccaagctagcaccacaagacagccccgactgaggatga caccccctcaaacatatggccggttacctcccaggtgat (SEQ ID NO: 48) | <u>GHM</u>FEGCHPQSGLSC<u>GASLVT</u> (SEQ ID NO: 62) | Pepenv24 Anti |

TABLE 5c

Primers for construction of gpIII/env2 with peptide insertions and to determine insert and orientation of hCAT1 peptide insertions BstEII site of ecotropic murine leukemia envelope

| Peptide insertion | Name | Strand | Sequence (5'- . . . -3') |
|---|---|---|---|
| FEQHNWWDSHPQ (SEQ ID NO: 20) | Pepenv25 | Sense | tgagcagcataattggtggg (SEQ ID NO: 53) |
| NTFDLWLQSVPQ (SEQ ID NO: 21) | Pepenv26 | Sense | ttgatctttggctgcagtct (SEQ ID NO: 54) |
| SVSVGMKPSPRP (SEQ ID NO: 1) | Pepenv27 | Sense | tctgtgggtatgaagccgag (SEQ ID NO: 55) |
| FEGCHPQSGLSC (SEQ ID NO: 22) | Pepenv28 | Sense | tttgaggggtgtcatcctca (SEQ ID NO: 56) |

| Priming site | Name | Strand | Sequence |
|---|---|---|---|
| 3' of PinA1 site in ecotropic envelope | Ecoenv05 | Antisense | gtcctagattttggtatctg (SEQ ID NO: 57) |
| Fusion envelope and pelB leader sequence protein m13, NotI site | Ecoenv17 | Sense | ctcgctcgcccatatgcggccgcaggtctcctcctcttagcagcacaacc agcaatggccgcttcgcccggctcc (SEQ ID NO: 58) |
| Fusion envelope and gIII protein m13, SpeI and SgrA1 site | Ecoenv12 | Antisense | agcatcactagtgccggtggaagttg (SEQ ID NO: 59) |

TABLE 6

Synthetic single stranded oligonucleotides used for PCR. Insertions of hCAT1 binding peptides in HI loop of Adenovirus serotype 5 are indicated by bold lowercase letters.

| Sequence (5'- . . . -3') | Peptide Insert | Name and orientation primers |
|---|---|---|
| ctgaggatgcgaatcccaccaattatgctgctcaaaAGTTGTGTCTCCTGTTTC (SEQ ID NO: 60) | FEQHNWWDSHPQ (SEQ ID NO: 20) | hCAD1AS-1 |
| tttgagcagcataattggtgggattcgcatcctcagCCAAGTGCATACTCTATG (SEQ ID NO: 61) | FEQHNWWDSHPQ (SEQ ID NO: 20) | hCAD1S-1 |
| ctgaggaacagactgcagccaaagatcaaaagtattAGTTGTGTCTCCTGTTTC (SEQ ID NO: 62) | NTFDLWLQSVPQ (SEQ ID NO: 21) | hCAD2AS-3 |
| aatactttgatctttggctgcagtctgttcctcagCCAAGTGCATACTCTATG (SEQ ID NO: 63) | NTFDLWLQSVPQ (SEQ ID NO: 21) | hCAD2S-4 |
| aggcctaggactcggcttcatacccacagaaacagaAGTTGTGTCTCCTGTTTC (SEQ ID NO: 64) | SVSVGMKPSPRP (SEQ ID NO: 1) | hCAD3AS-5 |
| tctgtttctgtgggtatgaagccgagtcctaggcctCCAAGTGCATACTCTATG (SEQ ID NO: 65) | SVSVGMKPSPRP (SEQ ID NO: 1) | hCAD3S-6 |
| acaagacagccccgactgaggatgacaccccctcaaaAGTTGTGTCTCCTGTTTC (SEQ ID NO: 66) | FEGCHPQSGLSC (SEQ ID NO: 22) | hCAD4AS-7 |
| tttgaggggtgtcatcctcagtcggggctgtcttgtCCAAGTGCATACTCTATG (SEQ ID NO: 67) | FEGCHPQSGLSC (SEQ ID NO: 22) | hCAD4S-8 |
| GCCGATGCATTTATTCTTGGGCAATGTATG (SEQ ID NO: 68) | Right AS | NsiIAd5-1 |
| CCCGTGTATCCATATGACACGGAAACCGGT (SEQ ID NO: 69) | Left S | NdeIAd5-1 |
| GGATACAGCGCCTTGCACTGTGG (SEQ ID NO: 70) | Right AS | Ad5-1rev1 |
| CGACATATGTAGATGCATTAGTTTGTGTTATGTTTCAACGTG (SEQ ID NO: 71) | NA | NY-up |
| GGAGACCACTGCCATGTTG (SEQ ID NO: 72) | NA | NY-down |

| | Primary PCR | Secondary PCR |
|---|---|---|
| | NdeIAd5-1/hCAD1AS-1 | NdeIAd5-1/NsiIAd5-1 |
| | NsiIAd5-1/hCAD1S-2 | NdeIAd5-1/NsiIAd5-1 |
| | NdeIAd5-1/hCAD2AS-3 | NdeIAd5-1/NsiIAd5-1 |
| | NsiIAd5-1/hCAD2S-4 | NdeIAd5-1/NsiIAd5-1 |
| | NdeIAd5-1/hCAD3AS-5 | NdeIAd5-1/NsiIAd5-1 |

TABLE 6-continued

Synthetic single stranded oligonucleotides used for PCR.Insertions of hCAT1 binding peptides in HI loop of Adenovirus serotype 5 are indicated by bold lowercase letters.

| | |
|---|---|
| NsiIAd5-1/hCAD3S-6 | NdeIAd5-1/NsiIAd5-1 |
| NdeIAd5-1/hCAD4AS-7 | NdeIAd5-1/NsiIAd5-1 |
| NsiIAD5-1/hCAD4S-8 | NdeIAd5-1/NsiIAd5-1 |

What is claimed is:

1. A virus-like particle or gene delivery vehicle provided with an amino acid ligand capable of binding to human cationic amino acid transporter-1 (hCAT1).

2. The virus-like particle or gene delivery vehicle of claim 1, wherein the amino acid ligand is provided with at least one viral protein.

3. The virus-like particle or gene delivery vehicle of claim 1, wherein said ligand comprises at least a part of the amino acid sequence SVSVGMKPSPRP (SEQ ID NO: 1).

4. The virus-like particle or gene delivery vehicle of claim 2 wherein said viral protein comprises an envelope protein.

5. The virus-like particle or gene delivery vehicle of claim 2 wherein said viral protein comprises a capsid protein.

6. The virus-like particle or gene delivery vehicle of claim 2, wherein said ligand comprises at least a part of the amino acid sequence SVSVGMKPSPRP (SEQ ID NO: 1).

7. The virus-like particle or gene delivery vehicle of claim 4, wherein said envelope protein is is of retroviral origin.

8. The virus-like particle or gene delivery vehicle of claim 4, wherein said ligand comprises at least a part of the amino acid sequence SVSVGMKPSPRP (SEQ ID NO: 1).

9. The virus-like particle or gene delivery vehicle of claim 7, wherein said ligand comprises at least a part of the amino acid sequence SVSVGMKPSPRP (SEQ ID NO: 1).

10. The virus-like particle or gene delivery vehicle of claim 5, wherein said capsid protein is of adenoviral origin.

11. The virus-like particle or gene delivery vehicle of claim 5, wherein said ligand comprises at least a part of the amino acid sequence SVSVGMKPSPRP (SEQ ID NO: 1).

12. The virus-like particle or gene delivery vehicle of claim 10, wherein said ligand comprises at least a part of the amino acid sequence SVSVGMKPSPRP (SEQ ID NO: 1).

* * * * *

UNITED STATES PATENT AND TRADEMARK OFFICE
CERTIFICATE OF CORRECTION

PATENT NO. : 6,498,027 B1
DATED : December 24, 2002
INVENTOR(S) : Helmuth Van Es et al.

It is certified that error appears in the above-identified patent and that said Letters Patent is hereby corrected as shown below:

Column 6,
Line 44, change "retroviru's" to -- retrovirus --

Column 7,
Line 31, change "residues;," to -- residues --

Column 9,
Line 51, change "Internet'i" to -- Internat'l --

Column 11,
Line 59, delete the period after "-specific"

Column 14,
Line 58, delete the colon after "envelope"

Column 17,
Line 61, change "pBr/Ad.BamRAFib" to -- pBr/Ad.BamRΔFib --

Column 18,
Line 66, change "fibS" to -- fib5 --

Column 19,
Line 6, change "pzipADMo+" to -- pZipΔDMo+ --
Line 46, change "Internet'l" to -- Internat'l --
Line 54, change "ClaI" to -- ClaI --

Column 20,
Lines 2 and 9, change "pAdS/Clip" to -- pAd5/Clip --
Line 10, change "pAdS/Clipsal" to -- pAd5/Clipsal --
Line 11, change "pAdS" to -- pAd5 --
Lines 28 and 31, change "SpeI" to -- SpeI --
Line 49, change "AdS" to -- Ad5 --

UNITED STATES PATENT AND TRADEMARK OFFICE
CERTIFICATE OF CORRECTION

PATENT NO. : 6,498,027 B1
DATED : December 24, 2002
INVENTOR(S) : Helmuth Van Es et al.

It is certified that error appears in the above-identified patent and that said Letters Patent is hereby corrected as shown below:

Column 21,
Line 26, change "Ndel" to -- NdeI -- and change "Nsil" to -- NsI --

Column 22,
Line 7, change "Hoogeriugge" to -- Hoogerbrugge --
Line 62, change "21 1." to -- 211. --

Signed and Sealed this

Sixteenth Day of September, 2003

JAMES E. ROGAN
*Director of the United States Patent and Trademark Office*

SEQUENCE LISTING

```
<160> NUMBER OF SEQ ID NOS: 81

<210> SEQ ID NO 1
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide
<221> NAME/KEY: PEPTIDE
<222> LOCATION: (1)..(12)
<223> OTHER INFORMATION: /note="hCat1 ligand"

<400> SEQUENCE: 1

Ser Val Ser Val Gly Met Lys Pro Ser Pro Arg Pro
1               5                   10

<210> SEQ ID NO 2
<211> LENGTH: 33
<212> TYPE: PRT
<213> ORGANISM: Homo sapiens
<220> FEATURE:
<221> NAME/KEY: PEPTIDE
<222> LOCATION: (1)..(33)
<223> OTHER INFORMATION: /note="hCat1 extracellular domain"

<400> SEQUENCE: 2

Lys Asn Trp Gln Leu Thr Glu Glu Asp Phe Gly Asn Thr Ser Gly Arg
1               5                   10                  15

Leu Cys Leu Asn Asn Asp Thr Lys Glu Gly Lys Pro Gly Val Gly Gly
            20                  25                  30

Phe

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)

<400> SEQUENCE: 3
ccctcatagt tagcgtaacg                                              20

<210> SEQ ID NO 4
<211> LENGTH: 47
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(47)
```

```
<223> OTHER INFORMATION: /note="Primer LTR-1"

<400> SEQUENCE: 4
ctgtacgtac cagtgcactg gcctaggcat ggaaaaatac ataactg        47

<210> SEQ ID NO 5
<211> LENGTH: 64
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(64)
<223> OTHER INFORMATION: /note="Primer LTR-2"

<400> SEQUENCE: 5
gcggatcctt cgaaccatgg taagcttggt accgctagcg ttaaccgggc gactcagtca        60
atcg                                                                     64

<210> SEQ ID NO 6
<211> LENGTH: 28
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(28)
<223> OTHER INFORMATION: /note="Primer HSA1"

<400> SEQUENCE: 6
gcgccaccat gggcagagcg atggtggc        28

<210> SEQ ID NO 7
<211> LENGTH: 50
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(50)
<223> OTHER INFORMATION: /note="Primer HSA2"

<400> SEQUENCE: 7
gttagatcta agcttgtcga catcgatcta ctaacagtag agatgtagaa        50

<210> SEQ ID NO 8
<211> LENGTH: 10
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(10)

<400> SEQUENCE: 8
ttaagtcgac        10

<210> SEQ ID NO 9
<211> LENGTH: 32
<212> TYPE: DNA
<213> ORGANISM: Artificial Sequence
<220> FEATURE:
<221> NAME/KEY: misc_feature
<223> OTHER INFORMATION: Description of Artificial Sequence: phage
```

```
<221> NAME/KEY: primer_bind
<222> LOCATION: (1)..(32)

<400> SEQUENCE: 9 gggtggcca gggtacctct aggcttttgc aa                              32

<210> SEQ ID NO 10
<211> LENGTH: 29
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(29)

<400> SEQUENCE: 10 gggggatcc ataaacaagt tcagaatcc                                  29

<210> SEQ ID NO 11
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 11

Glu Gln Ser Arg Pro Ser Trp Gln Leu Thr Pro Thr
1               5                   10

<210> SEQ ID NO 12
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 12

Gln Thr His Gln Leu Leu Arg Lys Pro Pro Ser Phe
1               5                   10

<210> SEQ ID NO 13
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 13

Tyr Met His Glu Pro Ile Thr Pro Asn Pro Val Thr
1               5                   10

<210> SEQ ID NO 14
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 14
```

```
Trp His His Ile Pro Asn Ser Ala Lys Ile Ser Leu
1               5                   10
```

```
<210> SEQ ID NO 15
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 15

Ser Glu Asn Leu Thr Leu Met Thr Val Leu Gln Met
1               5                   10
```

```
<210> SEQ ID NO 16
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 16

Asn Leu Met Pro Pro Pro Val Pro Arg Leu Pro Leu
1               5                   10
```

```
<210> SEQ ID NO 17
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 17

Thr Pro Gln Gly Val His Tyr His Pro Asn Met Arg
1               5                   10
```

```
<210> SEQ ID NO 18
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 18

Thr Leu Asn Asn His Thr Thr Pro Pro Ala Trp Asn
1               5                   10
```

```
<210> SEQ ID NO 19
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 19

Gln Val Val His Ser Pro Phe Pro Thr Ser Arg Pro
1               5                   10
```

<210> SEQ ID NO 20
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 20

Phe Glu Gln His Asn Trp Trp Asp Ser His Pro Gln
1               5                   10

<210> SEQ ID NO 21
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 21

Asn Thr Phe Asp Leu Trp Leu Gln Ser Val Pro Gln
1               5                   10

<210> SEQ ID NO 22
<211> LENGTH: 12
<212> TYPE: PRT
<213> ORGANISM: Artificial Sequence
<220> FEATURE:
<221> NAME/KEY: misc_feature
<223> OTHER INFORMATION: Description of Artificial Sequence: phage
      display peptide

<400> SEQUENCE: 22

Phe Glu Gly Cys His Pro Gln Ser Gly Leu Ser Cys
1               5                   10

<210> SEQ ID NO 23
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 23
tttgagcagc ataattggtg ggattcgcat cctcagcccc cggggccccc ttgt           54

<210> SEQ ID NO 24
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 24
ctgaggatgc gaatcccacc aattatgctg ctcaaaggat tgatattcta gccc           54

<210> SEQ ID NO 25
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 25
tttgagcagc ataattggtg ggattcgcat cctcagcggt gcaacactgc ctgg        54

<210> SEQ ID NO 26
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 26
ctgaggatgc gaatcccacc aattatgctg ctcaaaaggt tcttcgcagt ctct        54

<210> SEQ ID NO 27
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 27 aatactttg atctttggct gcagtctgtt cctcagcccc cggggccccc ttgt         54

<210> SEQ ID NO 28
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: protein_bind
<222> LOCATION: (1)..(54)

<400> SEQUENCE: 28
ctgaggaaca gactgcagcc aaagatcaaa agtattggat tgatattcta gccc        54

<210> SEQ ID NO 29
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 29 aatactttg atctttggct gcagtctgtt cctcagcggt gcaacactgc ctgg         54

<210> SEQ ID NO 30
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind -continued

```
<222> LOCATION: (1)..(54)

<400> SEQUENCE: 30
ctgaggaaca gactgcagcc aaagatcaaa agtattaggt tcttcgcagt ctct      54

<210> SEQ ID NO 31
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 31
tctgtttctg tgggtatgaa gccgagtcct aggcctcccc cggggccccc ttgt      54

<210> SEQ ID NO 32
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 32
aggcctagga ctcggcttca tacccacaga aacagaggat tgatattcta gccc      54

<210> SEQ ID NO 33
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 33
tctgtttctg tgggtatgaa gccgagtcct aggcctcggt gcaacactgc ctgg      54

<210> SEQ ID NO 34
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 34
aggcctagga ctcggcttca tacccacaga aacagaaggt tcttcgcagt ctct      54

<210> SEQ ID NO 35
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 35
``` tttgagggt gtcatcctca gtcggggctg tcttgtcccc cggggccccc ttgt        54

<210> SEQ ID NO 36
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 36
acaagacagc cccgactgag gatgacaccc ctcaaaggat tgatattcta gccc        54

<210> SEQ ID NO 37
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 37 tttgagggt gtcatcctca gtcggggctg tcttgtcggt gcaacactgc ctgg        54

<210> SEQ ID NO 38
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)

<400> SEQUENCE: 38
acaagacagc cccgactgag gatgacaccc ctcaaaaggt tcttcgcagt ctct        54

<210> SEQ ID NO 39
<211> LENGTH: 4
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      binding peptide

<400> SEQUENCE: 39

Pro Phe Ser Ser
1

<210> SEQ ID NO 40
<211> LENGTH: 6
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      binding peptide

<400> SEQUENCE: 40

Leu Thr Ser Leu Thr Pro
1               5

<210> SEQ ID NO 41

<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 41
atcacctggg aggtaaccgg ccatatgttt gagcagcata attggtggga ttcgcatcct    60
cagggtgcta gcttggtaac caatggagat cg                                 92

<210> SEQ ID NO 42
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 42
cgatctccat tggttaccaa gctagcaccc tgaggatgcg aatcccacca attatgctgc    60
tcaaacatat ggccggttac ctcccaggtg at                                 92

<210> SEQ ID NO 43
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 43
atcacctggg aggtaaccgg ccatatgaat acttttgatc tttggctgca gtctgttcct    60
cagggtgcta gcttggtaac caatggagat cg                                 92

<210> SEQ ID NO 44
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 44
cgatctccat tggttaccaa gctagcaccc tgaggaacag actgcagcca aagatcaaaa    60
gtattcatat ggccggttac ctcccaggtg at                                 92

<210> SEQ ID NO 45
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 45
atcacctggg aggtaaccgg ccatatgtct gtttctgtgg gtatgaagcc gagtcctagg    60
cctggtgcta gcttggtaac caatggagat cg    92

<210> SEQ ID NO 46
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 46
cgatctccat tggttaccaa gctagcacca ggcctaggac tcggcttcat acccacagaa    60
acagacatat ggccggttac ctcccaggtg at    92

<210> SEQ ID NO 47
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 47
atcacctggg aggtaaccgg ccatatgttt gaggggtgtc atcctcagtc ggggctgtct    60
tgtggtgcta gcttggtaac caatggagat cg    92

<210> SEQ ID NO 48
<211> LENGTH: 92
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(92)

<400> SEQUENCE: 48
cgatctccat tggttaccaa gctagcacca caagacagcc ccgactgagg atgacacccc    60
tcaaacatat ggccggttac ctcccaggtg at    92

<210> SEQ ID NO 49
<211> LENGTH: 21
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      binding peptide

<400> SEQUENCE: 49

Gly His Met Phe Glu Gln His Asn Trp Trp Asp Ser His Pro Gln Gly
1               5                   10                  15

Ala Ser Leu Val Thr
            20

<210> SEQ ID NO 50
<211> LENGTH: 21
<212> TYPE: PRT
<213> ORGANISM: Artificial Sequence
<220> FEATURE:

```
<221> NAME/KEY: misc_feature
<223> OTHER INFORMATION: Description of Artificial Sequence: hCAT1
      binding peptide

<400> SEQUENCE: 50

Gly His Met Asn Thr Phe Asp Leu Trp Leu Gln Ser Val Pro Gln Gly
1               5                   10                  15

Ala Ser Leu Val Thr
            20

<210> SEQ ID NO 51
<211> LENGTH: 21
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      binding peptide

<400> SEQUENCE: 51

Gly His Met Ser Val Ser Val Gly Met Lys Pro Ser Pro Arg Pro Gly
1               5                   10                  15

Ala Ser Leu Val Thr
            20

<210> SEQ ID NO 52
<211> LENGTH: 21
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      binding peptide

<400> SEQUENCE: 52

Gly His Met Phe Glu Gly Cys His Pro Gln Ser Gly Leu Ser Cys Gly
1               5                   10                  15

Ala Ser Leu Val Thr
            20

<210> SEQ ID NO 53
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)
<223> OTHER INFORMATION: /note="Primer for construction of gpIII/env2"

<400> SEQUENCE: 53
tgagcagcat aattggtggg                                           20

<210> SEQ ID NO 54
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)
<223> OTHER INFORMATION: /note="Primer for construction of gpIII/env2"

<400> SEQUENCE: 54
ttgatctttg gctgcagtct                                           20
```

<210> SEQ ID NO 55
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)
<223> OTHER INFORMATION: /note="Primer for construction of gpIII/env2"

<400> SEQUENCE: 55
tctgtgggta tgaagccgag                                          20

<210> SEQ ID NO 56
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)
<223> OTHER INFORMATION: /note="Primer for construction of gpIII/env2"

<400> SEQUENCE: 56
tttgaggggt gtcatcctca                                          20

<210> SEQ ID NO 57
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(20)
<223> OTHER INFORMATION: /note="Primer for construction of gpIII/env2"

<400> SEQUENCE: 57
gtcctagatt ttggtatctg                                          20

<210> SEQ ID NO 58
<211> LENGTH: 75
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(75)
<223> OTHER INFORMATION: /note="Primer for construction of gpIII/env2"

<400> SEQUENCE: 58
ctcgctcgcc catatgcggc cgcaggtctc ctcctcttag cagcacaacc agcaatggcc      60
gcttcgcccg gctcc                                                      75

<210> SEQ ID NO 59
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(27)
<223> OTHER INFORMATION: /note="Primer for construction of gpIII/env2"

-continued

```
<400> SEQUENCE: 59
agcatcacta gtcgccggtg gaagttg                                27

<210> SEQ ID NO 60
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD1AS-1"

<400> SEQUENCE: 60
ctgaggatgc gaatcccacc aattatgctg ctcaaaagtt gtgtctcctg tttc        54

<210> SEQ ID NO 61
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD1S-2"

<400> SEQUENCE: 61
tttgagcagc ataattggtg ggattcgcat cctcagccaa gtgcatactc tatg        54

<210> SEQ ID NO 62
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD2AS-3"

<400> SEQUENCE: 62
ctgaggaaca gactgcagcc aaagatcaaa agtattagtt gtgtctcctg tttc        54

<210> SEQ ID NO 63
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD2S-4"

<400> SEQUENCE: 63 aatactttttg atctttggct gcagtctgtt cctcagccaa gtgcatactc tatg        54

<210> SEQ ID NO 64
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD3AS-5"
```

```
<400> SEQUENCE: 64
aggcctagga ctcggcttca tacccacaga aacagaagtt gtgtctcctg tttc         54

<210> SEQ ID NO 65
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD3S-6"

<400> SEQUENCE: 65
tctgtttctg tgggtatgaa gccgagtcct aggcctccaa gtgcatactc tatg         54

<210> SEQ ID NO 66
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD4AS-7"

<400> SEQUENCE: 66
acaagacagc cccgactgag gatgacaccc ctcaaaagtt gtgtctcctg tttc         54

<210> SEQ ID NO 67
<211> LENGTH: 54
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(54)
<223> OTHER INFORMATION: /note="hCAD4S-8"

<400> SEQUENCE: 67 tttgagggt gtcatcctca gtcggggctg tcttgtccaa gtgcatactc tatg          54

<210> SEQ ID NO 68
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(30)
<223> OTHER INFORMATION: /note="NsiIAd5-1"

<400> SEQUENCE: 68
gccgatgcat ttattcttgg gcaatgtatg                                    30

<210> SEQ ID NO 69
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(30)
```

<223> OTHER INFORMATION: /note="NsiIAd5-1"

<400> SEQUENCE: 69
cccgtgtatc catatgacac ggaaaccggt                                    30

<210> SEQ ID NO 70
<211> LENGTH: 23
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(23)
<223> OTHER INFORMATION: /note="Ad5-1rev1"

<400> SEQUENCE: 70
ggatacagcg ccttgcactg tgg                                           23

<210> SEQ ID NO 71
<211> LENGTH: 42
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(42)
<223> OTHER INFORMATION: /note="NY-up"

<400> SEQUENCE: 71
cgacatatgt agatgcatta gtttgtgtta tgtttcaacg tg                      42

<210> SEQ ID NO 72
<211> LENGTH: 19
<212> TYPE: DNA
<213> ORGANISM: Homo sapiens
<220> FEATURE:
<221> NAME/KEY: misc_feature
<223> OTHER INFORMATION: Description of Artificial Sequence: phage
<221> NAME/KEY: primer_bind
<222> LOCATION: (1)..(19)
<223> OTHER INFORMATION: /note="NY-down"

<400> SEQUENCE: 72
ggagaccact gccatgttg                                                19

<210> SEQ ID NO 73
<211> LENGTH: 99
<212> TYPE: DNA
<213> ORGANISM: Homo sapiens
<220> FEATURE:
<221> NAME/KEY: CDS
<222> LOCATION: (1)..(99)
<223> OTHER INFORMATION: /note="third extracellular domain hCAT1 cDNA"

<400> SEQUENCE: 73 aaa aac tgg cag ctc acg gag gag gat ttt ggg aac aca tca ggc cgt     48
Lys Asn Trp Gln Leu Thr Glu Glu Asp Phe Gly Asn Thr Ser Gly Arg
1               5                   10                  15 ctc tgt ttg aac aat gac aca aaa gaa ggg aag ccc ggt gtt ggt gga     96
Leu Cys Leu Asn Asn Asp Thr Lys Glu Gly Lys Pro Gly Val Gly Gly
            20                  25                  30 ttc                                                                 99
Phe

<210> SEQ ID NO 74

```
<211> LENGTH: 33
<212> TYPE: PRT
<213> ORGANISM: Homo sapiens

<400> SEQUENCE: 74

Lys Asn Trp Gln Leu Thr Glu Glu Asp Phe Gly Asn Thr Ser Gly Arg
1               5                   10                  15

Leu Cys Leu Asn Asn Asp Thr Lys Glu Gly Lys Pro Gly Val Gly Gly
            20                  25                  30

Phe

<210> SEQ ID NO 75
<211> LENGTH: 33
<212> TYPE: PRT
<213> ORGANISM: Homo sapiens

<400> SEQUENCE: 75

Lys Asn Trp Gln Leu Thr Glu Glu Asp Phe Gly Asn Thr Ser Gly Arg
1               5                   10                  15

Leu Cys Leu Asn Asn Asp Thr Lys Glu Gly Lys Pro Gly Val Gly Gly
            20                  25                  30

Phe

<210> SEQ ID NO 76
<211> LENGTH: 27
<212> TYPE: PRT
<213> ORGANISM: Artificial Sequence
<220> FEATURE:
<221> NAME/KEY: misc_feature
<223> OTHER INFORMATION: Description of Artificial Sequence: hCAT1
      peptide

<400> SEQUENCE: 76

Lys Arg Arg Asn Asn Asp Thr Lys Glu Gly Lys Pro Gly Val Gly Gly
1               5                   10                  15

Phe Met Pro Phe Gly Phe Ser Gly Val Leu Ser
            20                  25

<210> SEQ ID NO 77
<211> LENGTH: 26
<212> TYPE: PRT
<213> ORGANISM: Artificial Sequence
<220> FEATURE:
<221> NAME/KEY: misc_feature
<223> OTHER INFORMATION: Description of Artificial Sequence: mCAT1
      peptide

<400> SEQUENCE: 77

Lys Arg Arg Asn Asn Asp Thr Asn Val Lys Tyr Gly Glu Gly Gly Phe
1               5                   10                  15

Met Pro Phe Gly Phe Ser Gly Val Leu Ser
            20                  25

<210> SEQ ID NO 78
<211> LENGTH: 5925
<212> TYPE: DNA
<213> ORGANISM: Artificial Sequence
<220> FEATURE:
<221> NAME/KEY: misc_feature
<223> OTHER INFORMATION: Description of Artificial Sequence: phage
<221> NAME/KEY: primer_bind
<222> LOCATION: (1)..(5925)
<223> OTHER INFORMATION: /note="Nucleotide hCAT1 encoding sequence

<400> SEQUENCE: 78
```

-continued

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttgtctc acccagaaac gctggtgaaa gtaaaagatg     300
ctgaagatca gttgggtgcc cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttaatt taaaaggatc taggtgaaga    1140
tcctttttga taatctcatg accaaaatcc cttaacgtga gttttcgttc cactgagcgt    1200 cagacccgt agaaaagatc aaaggatctt cttgagatcc ttttttctg cgcgtaatct    1260 gctgcttgca acaaaaaaa ccaccgctac cagcggtggt ttgtttgccg gatcaagagc    1320
taccaactct ttttccgaag gtaactggct tcagcagagc gcagatacca atactgtcc    1380 ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcataca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag    1800 gggggcggag cctatggaaa aacgccagca acgcggcctt tttacggttc ctggccttt    1860 gctggccttt tgctcacatg ttctttcctg cgttatcccc tgattctgtg ataaccgta    1920 ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcaccca ggctttacac tttatgcttc    2160
cggctcgtat gttgtgtgga attgtgagcg ataacaatt tcacacagga aacagctatg    2220
accatgatta cgccaagctt tggagccttt ttttggaga tttcaacgt gaaaaaatta    2280 ttattcgcaa ttcctttagt tgttcctttc tattctcaca gtgcacttga aacgacactc    2340
```

-continued

```
acgcagtctc caggcatcct gtctttgtct ccgggggcag gagccaccct ctcctgcagg    2400
gccagtcaga gtgtcagcag caggaactta gcctggtacc agcagaaacc tggccaggct    2460
cccaggctcc tcatctatgg tgtatccaac agggccactg gcgtcccaga caggttcagt    2520
ggcagtgggt ctggggcaga cttcactctc accatcaaca gactggagcc tgaagatttt    2580
gcggtgtatt actgtcagcg gtatggcagg tcactgtgga cgttcggtca agggaccaag    2640
gtggagatca aacgtggaac tgtggctgca ccatctgtct tcatcttccc gccatctgat    2700
gagcagttga aatctggaac tgcctctgtt gtgtgcctgc tgaataactt ctatcccaga    2760
gaggccaaag tacagtggaa ggtggataac gccctccaat cgggtaactc ccaggagagt    2820
gtcacagagc aggacagcaa ggacagcacc tacagcctca gcagcaccct gacgctgagc    2880
aaagcagact acgagaaaca caaagtctac gcctgcgaag tcacccatca gggcctgagt    2940
tcaccggtga caaagagctt caacagggga gagtgttaat aaggcgcgcc aattctattt    3000
caaggagaca gtcataatga aatacctatt gcctacggca gccgctggat tgttattact    3060
cgcggcccag ccggccatgg cccaggtcca gctggtgcag tctgggggag gcgtggtcca    3120
gcctgggagg tccctgagac tctcctgtgc agcctctgga ttcaccttca gtagctatgc    3180
tatgcactgg gtccgccagg ctccaggcaa ggggctggag tgggtggcag ttatatcata    3240
tgatggaagc aataaatact acgcagactc cgtgaagggc cgattcacca ctctccagag a    3300 caattccaag aacacgctgt atctgcaaat gaacagcctg agagctgagg acacggctgt    3360
gtattactgt gcgagaggga ttacagtaac taaatcacga tttgactact ggggccaggg    3420
caccctggtc accgtctcaa gcgcctccac caagggccca tcggtcttcc ccctggcacc    3480
ctcctccaag agcacctctg gggcacagc ggccctgggc tgcctggtca aggactactt    3540
ccccgaaccg gtgacggtgt cgtggaactc aggcgccctg accagcggcg tccacacctt    3600
cccggctgtc ctacagtcct caggactcta ctccctcagc agcgtagtga ccgtgccctc    3660
cagcagcttg ggcacccaga cctacatctg caacgtgaat cacaagccca gcaacaccaa    3720
ggtggacaag aaagttgagc ccaaatcttg tgcggccgca catcatcatc accatcacgg    3780
ggccgcagaa caaaaactca tctcagaaga ggatctgaat ggggccgcat agactgttga    3840
aagttgttta gcaaaacctc atacagaaaa ttcatttact aacgtctgga agacgacaa    3900 aactttagat cgttacgcta actatgaggg ctgtctgtgg aatgctacag gcgttgtggt    3960
ttgtactggt gacgaaactc agtgttacg tacatgggtt cctattgggc ttgctatccc    4020
tgaaaatgag ggtggtggct ctgagggtgg cggttctgag ggtggcggtt ctgagggtgg    4080
cggtactaaa cctcctgagt acggtgatac acctattccg ggctatactt atatcaaccc    4140
tctcgacggc acttatccgc ctggtactga gcaaaacccc gctaatccta atccttctct    4200
tgaggagtct cagcctctta atactttcat gtttcagaat aataggttcc gaaataggca    4260
gggtgcatta actgtttata cgggcactgt tactcaaggc actgaccccg ttaaaactta    4320
ttaccagtac actcctgtat catcaaaagc catgtatgac gcttactgga acggtaaatt    4380
cagagactgc gctttccatt ctggctttaa tgaggatcca ttcgtttgtg aatatcaagg    4440
ccaatcgtct gacctgcctc aacctcctgt caatgctggc ggcggctctg gtggtggttc    4500
tggtggcggc tctgagggtg cggctctga gggtggcggt tctgagggtg cggctctga    4560 gggtggcggt tccggtggcg ctccggttc cggtgatttt gattatgaaa aaatggcaaa    4620
cgctaataag gggctatga ccgaaaatgc cgatgaaaac gcgctacagt ctgacgctaa    4680
aggcaaactt gattctgtcg ctactgatta cggtgctgct atcgatggtt tcattggtga    4740
```

```
cgtttccggc cttgctaatg gtaatggtgc tactggtgat tttgctggct ctaattccca    4800
aatggctcaa gtcggtgacg gtgataattc acctttaatg aataatttcc gtcaatattt    4860
accttctttg cctcagtcgg ttgaatgtcg cccttatgtc tttggcgctg gtaaaccata    4920
tgaattttct attgattgtg acaaaataaa cttattccgt ggtgtctttg cgtttctttt    4980
atatgttgcc acctttatgt atgtattttc gacgtttgct aacatactgc gtaataagga    5040
gtcttaataa gaattcactg gccgtcgttt tacaacgtcg tgactgggaa aaccctggcg    5100
ttacccaact taatcgcctt gcagcacatc cccctttcgc cagctggcgt aatagcgaag    5160
aggcccgcac cgatcgccct tcccaacagt tgcgcagcct gaatggcgaa tggcgcctga    5220
tgcggtattt tctccttacg catctgtgcg gtatttcaca ccgcatataa attgtaaacg    5280
ttaatatttt gttaaaattc gcgttaaatt tttgttaaat cagctcattt tttaaccaat    5340
aggccgaaat cggcaaaatc ccttataaat caaagaata gcccgagata gggttgagtg    5400
ttgttccagt ttggaacaag agtccactat taagaacgt ggactccaac gtcaaagggc    5460
gaaaaaccgt ctatcagggc gatggcccac tacgtgaacc atcacccaaa tcaagttttt    5520
tggggtcgag gtgccgtaaa gcactaaatc ggaaccctaa agggagcccc cgatttagag    5580
cttgacgggg aaagccggcg aacgtggcga gaaggaagg gaagaaagcg aaaggagcgg    5640
gcgctagggc gctggcaagt gtagcggtca cgctgcgcgt aaccaccaca cccgccgcgc    5700
ttaatgcgcc gctacagggc gcgtactatg gttgctttga cgggtgcagt ctcagtacaa    5760
tctgctctga tgccgcatag ttaagccagc cccgacaccc gccaacaccc gctgacgcgc    5820
cctgacgggc ttgtctgctc ccggcatccg cttacagaca agctgtgacc gtctccggga    5880
gctgcatgtg tcagaggttt tcaccgtcat caccgaaacg cgcga    5925
```

<210> SEQ ID NO 79
<211> LENGTH: 236
<212> TYPE: PRT
<213> ORGANISM: Artificial Sequence
<220> FEATURE:
<221> NAME/KEY: misc_feature
<223> OTHER INFORMATION: Description of Artificial Sequence: phage
<221> NAME/KEY: PEPTIDE
<222> LOCATION: (1)..(236)
<223> OTHER INFORMATION: /note="hCAT1 amino acid sequence"

<400> SEQUENCE: 79

```
Val Lys Lys Leu Leu Phe Ala Ile Pro Leu Val Val Pro Phe Tyr Ser
  1               5                  10                  15

His Ser Ala Leu Glu Thr Thr Leu Thr Gln Ser Pro Gly Ile Leu Ser
             20                  25                  30

Leu Ser Pro Gly Ala Gly Ala Thr Leu Ser Cys Arg Ala Ser Gln Ser
         35                  40                  45

Val Ser Ser Arg Asn Leu Ala Trp Tyr Gln Gln Lys Pro Gly Gln Ala
     50                  55                  60

Pro Arg Leu Leu Ile Tyr Gly Val Ser Asn Arg Ala Thr Gly Val Pro
 65                  70                  75                  80

Asp Arg Phe Ser Gly Ser Gly Ser Gly Ala Asp Phe Thr Leu Thr Ile
                 85                  90                  95

Asn Arg Leu Glu Pro Glu Asp Phe Ala Val Tyr Tyr Cys Gln Arg Tyr
            100                 105                 110

Gly Arg Ser Leu Trp Thr Phe Gly Gln Gly Thr Lys Val Glu Ile Lys
        115                 120                 125
```

```
Arg Gly Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 80
<211> LENGTH: 248
<212> TYPE: PRT
<213> ORGANISM: Artificial Sequence
<220> FEATURE:
<221> NAME/KEY: misc_feature
<223> OTHER INFORMATION: Description of Artificial Sequence: phage
<221> NAME/KEY: PEPTIDE
<222> LOCATION: (1)..(248)
<223> OTHER INFORMATION: /note="hCAT1 amino acid sequence"

<400> SEQUENCE: 80

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Gly Gly
                20                  25                  30

Val Val Gln Pro Gly Arg Ser Leu Arg Leu Ser Cys Ala Ala Ser Gly
            35                  40                  45

Phe Thr Phe Ser Ser Tyr Ala Met His Trp Val Arg Gln Ala Pro Gly
    50                  55                  60

Lys Gly Leu Glu Trp Val Ala Val Ile Ser Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
                100                 105                 110

Thr Ala Val Tyr Tyr Cys Ala Arg Gly Ile Thr Val Thr Lys Ser Arg
            115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240
```

```
Glu Pro Lys Ser Cys Ala Ala Ala
            245

<210> SEQ ID NO 81
<211> LENGTH: 6
<212> TYPE: PRT
<213> ORGANISM: Artificial Sequence
<220> FEATURE:
<221> NAME/KEY: misc_feature
<223> OTHER INFORMATION: Description of Artifical Sequence: phage
<221> NAME/KEY: PEPTIDE
<222> LOCATION: (1)..(6)
<223> OTHER INFORMATION: /note="hCAT1 amino acid sequence"

<400> SEQUENCE: 81

His His His His His His
1               5
```